United States Patent
Megerian et al.

(10) Patent No.: US 11,735,320 B2
(45) Date of Patent: Aug. 22, 2023

(54) DYNAMIC CREATION AND MANIPULATION OF DATA VISUALIZATIONS

(71) Applicant: International Business Machines Corporation, Armonk, NY (US)

(72) Inventors: Mark Gregory Megerian, Rochester, MN (US); Fernando Jose Suarez Saiz, Armonk, NY (US); Thomas J. Eggebraaten, Rochester, NY (US); Marie Louise Setnes, Bloomington, MN (US)

(73) Assignee: MERATIVE US L.P., Ann Arbor, MI (US)

( * ) Notice: Subject to any disclaimer, the term of this patent is extended or adjusted under 35 U.S.C. 154(b) by 1120 days.

(21) Appl. No.: 16/208,838

(22) Filed: Dec. 4, 2018

(65) Prior Publication Data
US 2020/0176113 A1    Jun. 4, 2020

(51) Int. Cl.
*G16H 50/20* (2018.01)
*G06N 5/02* (2023.01)
*G16H 20/00* (2018.01)
*G06F 16/901* (2019.01)
(Continued)

(52) U.S. Cl.
CPC .......... *G16H 50/20* (2018.01); *G06F 16/9027* (2019.01); *G06N 5/02* (2013.01); *G16H 20/00* (2018.01); *G16H 50/70* (2018.01); *G16H 70/20* (2018.01)

(58) Field of Classification Search
CPC ... G06F 1/00–2221/2153; G16H 10/00–80/00; G06N 3/00–99/007
See application file for complete search history.

(56) References Cited

U.S. PATENT DOCUMENTS 7,184,963 B1 *   2/2007   Shannon ............... G16H 40/63
                                                600/557
10,665,343 B1 *   5/2020   Davenport ............ G06N 5/045
(Continued)

FOREIGN PATENT DOCUMENTS

WO   WO-2007005622 A2 *   1/2007   ............. A61K 49/00
WO      2014117873 A1    8/2014
WO   WO-2016115154 A1 *   7/2016   ............. A63F 13/28

OTHER PUBLICATIONS

Khan et al., "Artificial Intelligence based Smart Doctor using Decision Tree Algorithm," Journal of Information & Communication Technology—JICT vol. 11 Issue. (Year: 2017).*
(Continued)

*Primary Examiner* — Jonathon A. Szumny
(74) *Attorney, Agent, or Firm* — Patterson + Sheridan, LLP

(57) ABSTRACT

Techniques for dynamic visualization of data are provided. A plurality of therapies is received, where each of the plurality of therapies is associated with a respective plurality of guidelines. A guideline tree is generated based on the plurality of therapies, where each leaf node in the guideline tree represents a respective therapy, and where each edge in the guideline tree represents a respective guideline. A visual depiction of the guideline tree is generated. Further, a first plurality of attributes associated with a first patient is received, and a first modified visual depiction of the guideline tree is generated based on the first plurality of attributes.

16 Claims, 13 Drawing Sheets

(51) Int. Cl.
*G16H 50/70* (2018.01)
*G16H 70/20* (2018.01)

(56) References Cited

U.S. PATENT DOCUMENTS

| | | | | |
|---|---|---|---|---|
| 2002/0091687 | A1* | 7/2002 | Eglington | G16H 50/20 707/999.005 |
| 2013/0006649 | A1* | 1/2013 | Rangadass | G16H 40/20 705/2 |
| 2013/0035956 | A1* | 2/2013 | Carmeli | G06Q 10/10 705/3 |
| 2013/0174084 | A1 | 7/2013 | Lord et al. | |
| 2014/0088988 | A1* | 3/2014 | Fairbrothers | G16H 10/60 705/2 |
| 2014/0108040 | A1 | 4/2014 | Belcher et al. | |
| 2014/0201627 | A1* | 7/2014 | Freeman | G16H 40/63 715/771 |
| 2014/0337306 | A1* | 11/2014 | Gramatica | G06F 16/93 707/706 |
| 2015/0073831 | A1* | 3/2015 | Seaborn | G16H 20/00 705/3 |
| 2015/0238270 | A1* | 8/2015 | Raffy | A61B 90/37 600/407 |
| 2015/0254429 | A1* | 9/2015 | Belcher | G16Z 99/00 705/3 |
| 2015/0324402 | A1* | 11/2015 | Carmeli | G06N 20/00 705/2 |
| 2016/0321402 | A1* | 11/2016 | Zhou | G16H 50/20 |
| 2018/0046764 | A1* | 2/2018 | Katwala | G16H 15/00 |
| 2018/0294051 | A1* | 10/2018 | Dawes | G16H 20/30 |
| 2021/0407694 | A1* | 12/2021 | Deckert | G16H 15/00 |

OTHER PUBLICATIONS

Abdullahi et al., "On the Use of Decision Tree for Treatment Options in Medical Decision," International Journal of Advanced Research in Computer Science and Software Engineering, vol. 5, Issue 2, Feb. 2015 (Year: 2015).*

Krahn et al., "Visualizing inconsistency in network meta-analysis by independent path decomposition," Krahn et al. BMC Medical Research Methodology 2014, 14:131; http://www.biomedcentral.com/1471-2288/14/131. (Year: 2014).*

Shi et al., "Semantic Health Knowledge Graph: Se mantic Integration of Heterogeneous Medical Knowledge and Services," BioMed Research International, vol. 2017, Article ID 2858423, 12 pages; https://doi.org/10.1155/2017/2858423 (Year: 2017).*

Morid et al., "Classification of Clinically Useful Sentences in Clinical Evidence Resources," J Biomed Inform. Apr. 2016 ; 60: 14-22. doi:10.1016/j.jbi.2016.01.003. (Year: 2016).*

Fiszman et al., "Interpreting Comparative Constructions in Biomedical Text," BioNLP 2007: Biological, translational, and clinical language processing, pp. 137-144, Prague, Jun. 2007. (Year: 2007).*

Interactive Information Visualization to Explore and Query Electronic Health Records, Rind, A. et al.; 2013.

Progressive Personalization for Clinical Treatments Visualization, Anonymously; Oct. 8, 2015.

User Interface Data Visualization and Framework for Diabetes Care, Anonymously; Aug. 15, 2014.

Dynamic Multi-Language Translation for Medical Applications, Anonymously; Jan. 8, 2013.

* cited by examiner

DYNAMIC CREATION AND MANIPULATION OF DATA VISUALIZATIONS

BACKGROUND

The present disclosure relates to data processing and visualization, and more specifically, to generating and manipulating visualizations to enable deeper understanding of interactions in the data.

In a variety of domains, studies, experiments, and trials are performed to understand how potential options or selections interact and compare to each other. For example, in the medical field, studies and trials are performed to determine the efficacy of new and existing therapies, in order to determine the best practices for treating or curing illnesses or disorders. Frequently, the results of these studies, experiments, and trials are published for review by others. Currently, the published literature is reviewed manually by subject-matter experts (SMEs) to determine the state of the field, and provide guidance with respect to optimal therapies. However, these determinations are time-consuming, expensive, and inherently biased. Further, the published literature is expanding at an increasing and unprecedented rate. As the number of published documents increases, it has become impossible to aggregate and interpret them all. Thus, current guidelines and best practices are universally outdated, and potentially conflict with newly discovered therapies or interactions.

Additionally, when patients are to be treated, healthcare providers rely on the defined guidelines in order to determine which treatments or therapies are appropriate for a given patient. However, given the rapid pace and complexity of the published literature, as well as the enormous amount of data that must be considered, it is impossible for healthcare providers to identify and evaluate all of these potential therapies in view of their respective guidelines. Thus, patient outcomes are often worse than they could be.

SUMMARY

According to one embodiment of the present disclosure, a method is provided. The method includes receiving a plurality of therapies, wherein each of the plurality of therapies is associated with a respective plurality of guidelines. The method further includes generating a guideline tree based on the plurality of therapies, wherein each leaf node in the guideline tree represents a respective therapy, and wherein each edge in the guideline tree represents a respective guideline. Additionally, the method includes generating a visual depiction of the guideline tree. The method also includes receiving a first plurality of attributes associated with a first patient, and generating a first modified visual depiction of the guideline tree based on the first plurality of attributes.

According to a second embodiment of the present disclosure, a computer-readable storage medium is provided. The computer-readable storage medium has computer-readable program code embodied therewith, the computer-readable program code executable by one or more computer processors to perform an operation. The operation includes receiving a plurality of therapies, wherein each of the plurality of therapies is associated with a respective plurality of guidelines. The operation further includes generating a guideline tree based on the plurality of therapies, wherein each leaf node in the guideline tree represents a respective therapy, and wherein each edge in the guideline tree represents a respective guideline. Additionally, the operation includes generating a visual depiction of the guideline tree. The operation also includes receiving a first plurality of attributes associated with a first patient, and generating a first modified visual depiction of the guideline tree based on the first plurality of attributes.

According to a third embodiment of the present disclosure, a system is provided. The system includes one or more computer processors, and a memory containing a program which when executed by the one or more computer processors performs an operation. The operation includes receiving a plurality of therapies, wherein each of the plurality of therapies is associated with a respective plurality of guidelines. The operation further includes generating a guideline tree based on the plurality of therapies, wherein each leaf node in the guideline tree represents a respective therapy, and wherein each edge in the guideline tree represents a respective guideline. Additionally, the operation includes generating a visual depiction of the guideline tree. The operation also includes receiving a first plurality of attributes associated with a first patient, and generating a first modified visual depiction of the guideline tree based on the first plurality of attributes.

DETAILED DESCRIPTION

In one embodiment of the present disclosure, a guideline tree is generated based on published literature in order to provide a visualization of how different therapies relate to each other, and how various attributes of the patient contribute to the ultimate recommendation of a particular therapy. In embodiments, the structure of the visualization enables users (e.g., healthcare providers) to readily determine other therapies that may be useful (e.g., if one or more attributes can be changed), as well as which attributes should be adjusted. Further, in an embodiment, the visualization can be utilized to dynamically represent multiple patients, in order to provide a deeper understanding of how the patients differ, and why the therapy suggestions diverge. In one embodiment, the attributes of a single patient can be obtained at different points in time, in order to visualize how the patient's condition has evolved, as well as how and why the ideal therapy has shifted. Further, in some embodiments, guidelines at various points in time (or from various sources) can be used to generate visualizations illustrating how our understanding has shifted over time, or how various sources of knowledge differ with respect to their treatment recommendations.

In an embodiment, the guideline tree is generated such that each leaf node in the tree corresponds to a therapy option, and the remaining nodes (e.g., the internal nodes and root node) are each associated with an attribute that drives treatment decisions. In an embodiment each edge in the guideline tree is generated based on the published literature. In various embodiments, this can include established guidelines and best practices, analysis of a knowledge graph, evaluation of real-world evidence (RWE) through electronic medical records (EMRs), and the like. In an embodiment, the guideline tree can be navigated by beginning at the root node and, for each node in the tree, selecting the edge that the index patient matches. For example, a node may be associated with "age," and the edges from the node can apply to individuals who are "under 35," "35 to 65," and "over 65." Of course, in embodiments, there may be any number of edges from a given node.

Figure 1:
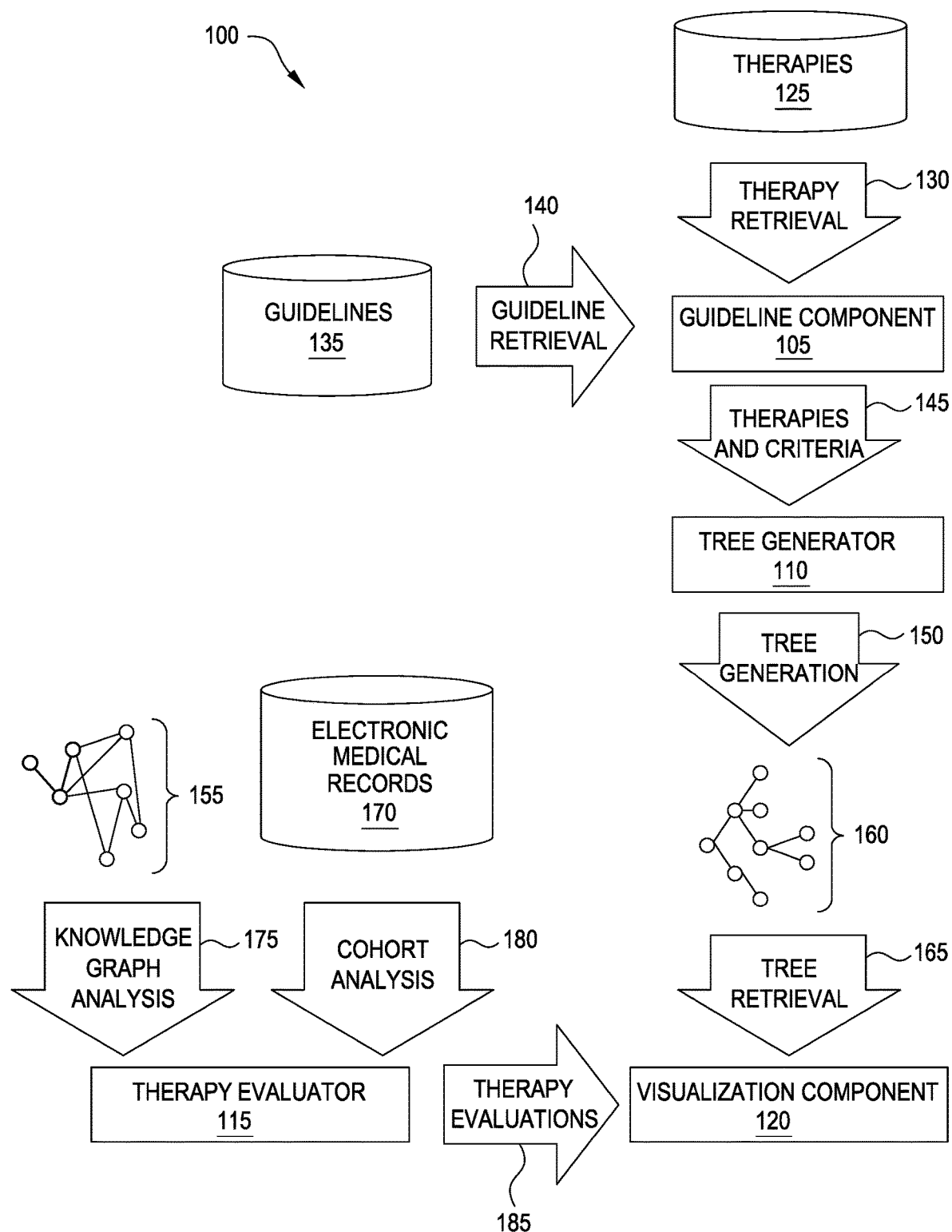
FIG. 1 illustrates a workflow for generating and manipulating a guideline tree, according to one embodiment disclosed herein.

FIG. 1 illustrates a workflow 100 for generating and manipulating a guideline tree, according to one embodiment disclosed herein. In the illustrated embodiment, a Guideline Component 105 performs Therapy Retrieval 130 to access a data store of Therapies 125. In one embodiment, the Therapies 125 are treatments associated with a particular disorder or condition. In some embodiments, the Guideline Component 105 identifies and retrieves these Therapies 125 based on an index patient (e.g., based on the attributes and/or condition of the index patient). In some embodiments, the Guideline Component 105 retrieves Therapies 125 for several disorders or conditions, and one or more guideline trees are generated for each disorder. In one embodiment, the Guideline Component 105 identifies these Therapies 135 in a knowledge graph that includes therapies and the relationships among the various potential therapies, as explained in more detail below.

Further, as illustrated, the Guideline Component 105 accesses a data store including Guidelines 135 in order to perform Guideline Retrieval 140. In an embodiment, the Guidelines 135 are rules, guidance, or instructions regarding whether a therapy or treatment is appropriate or useful for a given patient. In one embodiment, each of the Therapies 125 is associated with one or more Guidelines 135. In some embodiments, the Guidelines 135 are curated by subject-matter experts (SMEs), and are periodically updated. Although illustrated as residing in separate data stores, in an embodiment, the Guidelines 135 and Therapies 125 may be stored together or spread across any number of locations. In one embodiment, as discussed in more detail below, the Guideline Component 105 also analyzes other sources of data, such as the knowledge graph and/or EMRs, to generate additional guidance or criteria that are not reflected in the Guidelines 135. For example, in one embodiment, the Guideline Component 105 evaluates EMRs using one or more machine learning models to identify patient attributes that have historically driven treatment decisions (e.g., attributes that cause the treating physician to select a different therapy). In an embodiment, these identified attributes are included in the Guidelines 135 when generating the guideline tree. In some embodiments, the Guideline Component 105 analyzes EMRs and/or a knowledge graph to identify attributes that appear to influence the outcome of treatment, even if it was not considered when selecting the treatment. In such an embodiment, the guideline tree can further be generated or refined based on these identified attributes.

In the illustrated workflow 100, the Guideline Component 105 then passes these Therapies and Criteria 145 to a Tree Generator 110. That is, the Guideline Component 105 provides an indication as to the identified Therapies 125 that are to be used when generating the guideline tree (e.g., based on the disorder and/or patient to be treated). Further, as illustrated, for each of the Therapies 125 being used, the Guideline Component 105 indicates the corresponding guidelines and/or criteria (e.g., the attributes or factors that are considered when determining whether the therapy is appropriate or useful). The Tree Generator 110 then performs Tree Generation 150 to generate a Guideline Tree 160. In the illustrated embodiment, each leaf node in the Guideline Tree 160 corresponds to one of the indicated Therapies 125, and each edge corresponds to one of the indicated Guidelines 135 or criteria. Note that in some embodiments, a single leaf node may correspond to multiple therapies (e.g., if there is no differentiation in the attributes between them). In this way, the Guideline Tree 160 can be analyzed to quickly identify a suggested therapy for an index patient by, iteratively determining which attribute is implicated by the current selected node (e.g., the attribute that the corresponding edges relate to), and selecting the appropriate edge (based on the attributes of the index patient) to move to the next node until a leaf node is reached.

In the illustrated embodiment, a Visualization Component 120 then performs Tree Retrieval 165 to receive the Guideline Tree 160 from the Tree Generator 110 (or from a storage location), and generates a visualization of the tree. In one embodiment, the visualization is a graphical representation of the tree, displayed on a graphical user interface (GUI) of a user. Based on this visualization, the user can more readily grasp how the therapies are related, based on their corresponding guidelines or criteria for treatment. Further, in embodiments, this visualization can be modified and updated to reflect the attributes of one or more patients at one or more points in time, in order to visualize the attributes that led to the suggested therapy or therapies, as well as how patients compare (against each other, and against themselves over time). Additionally, in one embodiment, the Guideline Tree 160 can be periodically refined, and visualizations can be generated to illustrate how the current tree has evolved and changed from past trees (e.g., due to updated Guidelines 135).

In the illustrated embodiment, a Therapy Evaluator 115 performs Knowledge Graph Analysis 175 on a Knowledge Graph 155, as well as Cohort Analysis 180 on a corpus of Electronic Medical Records 170. In one embodiment, Knowledge Graph Analysis 175 involves analyzing a Knowledge Graph 155 based on attributes associated with the index patient (e.g., the patient to be treated) in order to score and rank potential therapies, based on their predicted efficacies. Further, in an embodiment, Cohort Analysis 180 includes analyzing EMRs 170 to determine a recommended therapy, based on RWE. In one embodiment, Cohort Analysis 180 first includes identifying a cohort of similar patients to the index patient, based on their attributes. The Therapy Evaluator 115 then identifies EMRs 170 that correspond to these patients, and determines which therapy was selected to treat the patient, as well as what the outcome was. In this way, the Therapy Evaluator 115 can provide one or more recommended therapies, based on what therapies have been historically selected, as well as which therapies were successful.

In some embodiments, the Therapy Evaluator 115 provides multiple suggested therapies. In one embodiment, the Therapy Evaluator 115 provides the best therapy, as determined by the Knowledge Graph Analysis 175 (e.g., based on published literature), as well as the best therapy, as determined by the Cohort Analysis 180 (e.g., based on RWE). In some embodiments, the Therapy Evaluator 115 determines an overall optimal therapy by combining or aggregating the Knowledge Graph Analysis 175 and Cohort Analysis 180, as discussed in more detail below. In the illustrated embodiment, the Therapy Evaluator 115 then provides these Therapy Evaluations 185 to the Visualization Component 120, which generates or updates the visualization of the Guideline Tree 160. For example, in one embodiment, the Visualization Component 120 determines the suggested or recommended therapies evaluated by the Therapy Evaluator 115, and locates them in the Guideline Tree 160.

In one embodiment, in addition to emphasizing or highlighting the therapy or therapies in the Guideline Tree 160 that are identified based on the Guidelines 135, the Visualization Component 120 can also highlight or emphasize the determined optimal therapies in the Therapy Evaluations 185. For example, in an embodiment, the Visualization Component 120 can determine a suggested therapy by traversing the Guideline Tree 160 comparing the patient's attributes to the Guidelines 135, and emphasize this determined therapy and/or path through the tree. In one embodiment, the Visualization Component 120 also emphasizes the determined optimal therapies (if it differs from the guideline-based therapy). In this way, the user can easily determine how the optimal therapy differs from the guideline-recommended therapy. In some embodiments, the Visualization Component 120 also emphasizes the node where the paths diverged between the optimal therapy and the suggested therapy. This can allow the user to understand which attribute(s) of the index patient caused the Guidelines 135 to recommend a different treatment.

In some embodiments, based on this modified visualization and/or Guideline Tree 160, the user or another component can determine whether these key attributes can be modified in order to shift the recommended therapy to align with the optimal therapy. For example, suppose the index patient consumes alcohol. Suppose further that, as between a therapy A and therapy B, the Guidelines 135 state that therapy A is recommended for those who consume alcohol, while therapy B is better for those who do not. Based on the fact that the index patient consumes alcohol, the suggested therapy per the Guideline Tree 160 will be therapy A. However, if the Therapy Evaluator 115 recommends therapy B as the more optimal treatment, the user can quickly determine, based on the visualization, that the node where the paths diverge relates to alcohol use. In this way, the dynamic visualization allows the user to readily determine that if the index patient ceases alcohol consumption, the guidelines will suggest therapy B, which the Therapy Evaluator 115 indicates will be a superior treatment.

In some embodiments of the present disclosure, as discussed above, a knowledge graph is analyzed to identify ideal or optimal therapies for patients. In an embodiment, the guideline tree is then updated based on this determination. In one embodiment of the present disclosure, the knowledge graph is created via various techniques for cognitive analysis, representation, and interpretation of published literature. In one embodiment, a corpus of medical literature is parsed and analyzed to identify and extract comparative statements or opinions made by the authors of the paper. For example, in a conclusion or summary, the authors may indicate that a particular therapy showed improved results, as compared to one or more other therapies (or as compared to the known or popular literature and practices). These conclusions are provided in natural language text, and are rarely structured in a way that allows for easy ingestion of the information. Embodiments of the present disclosure are discussed with reference to medical literature. However, these examples are not limiting on the present disclosure, and one of skill in the art will recognize other domains and literature that the present embodiments can be applied to.

In one embodiment, these comparative statements are interpreted to determine a sentiment of the statement, and the relative efficacy of each therapy discussed. In some embodiments, a data structure, referred to herein as a relative efficacy structure or RES, is generated to capture the natural language comparative statement in a useful format. For example, in one embodiment, the RES has a number of dimensions, including the directionality of the comparison (e.g., which therapy is superior), the magnitude of the difference, the particular outcome the statement refers to (e.g., survival, progression-free survival, remission, etc.), qualifiers of the statement (e.g., limitations or specifications), and the like. In an embodiment, each RES is also associated with a weight, which is based on a variety of factors related to the underlying comparative statement and the nature of the article it is contained in.

In one embodiment, if a comparison is found in one direction (e.g., that treatment A is better than treatment B), a complementary RES is created in the opposite direction (e.g., indicating that treatment B is worse than treatment A). In this way, queries for information for a given treatment or therapy can identify all documents that involve the therapy, regardless of whether the document deemed the therapy to be superior or inferior.

In some embodiments, a knowledge graph can be generated based on the determined relationships extracted from one or more published document. For example, in one embodiment, each node in the knowledge graph corresponds to a particular therapy, and each edge corresponds to one or more RESs. In this way, the knowledge graph can be interrogated or searched to identify optimal treatment options for a given patient, based on a tremendous variety of medical literature. In such an embodiment, patient outcomes are improved, as the current state of the literature can be captured and ingested into the knowledge graph rapidly, reducing or eliminating the need for SME review. Further, in embodiments, the RESs provide additional insight and knowledge that is not accessible or present in existing solutions. Thus, embodiments of the present disclosure enable high-precision searching, and allow users to analyze the literature at a more granular level.

In some embodiments, users can search or query the knowledge graph based on therapies, cohorts, disorders, and the like, to return a subset of the graph that is relevant to the search. Further, in some embodiments, nodes and/or connections can be selected to retrieve a link to any documents or published literature that was analyzed to create the node or edge. In this way, users can readily access the relevant literature, if they wish to investigate further or obtain more information about why the topology of the graph is shaped as it is, as well as why particular connections exist.

Embodiments of the present disclosure can be applied to extract and interpret comparative statements made in any field. In one embodiment, medical literature (e.g., published studies, trials, experiments, and the like) is ingested. In some embodiments, the literature is analyzed to identify comparisons or statements about relative efficacy between therapy options. In an embodiment, a therapy is any treatment used to treat a disorder. As used herein, therapies can include drugs, medications, exercises, surgeries, use of equipment, prescribed activities, and the like. Further, in embodiments, therapies can include refraining from certain activities and withdrawing or reducing treatments. Additionally, in embodiments, a therapy may include multiple treatments or prescribed activities (e.g., multiple medications). As used herein, a medical disorder can include any illness or medical condition, including but not limited to mental or physical disease, sickness, disability, infection, symptoms, conditions, or statuses.

Figure 2:
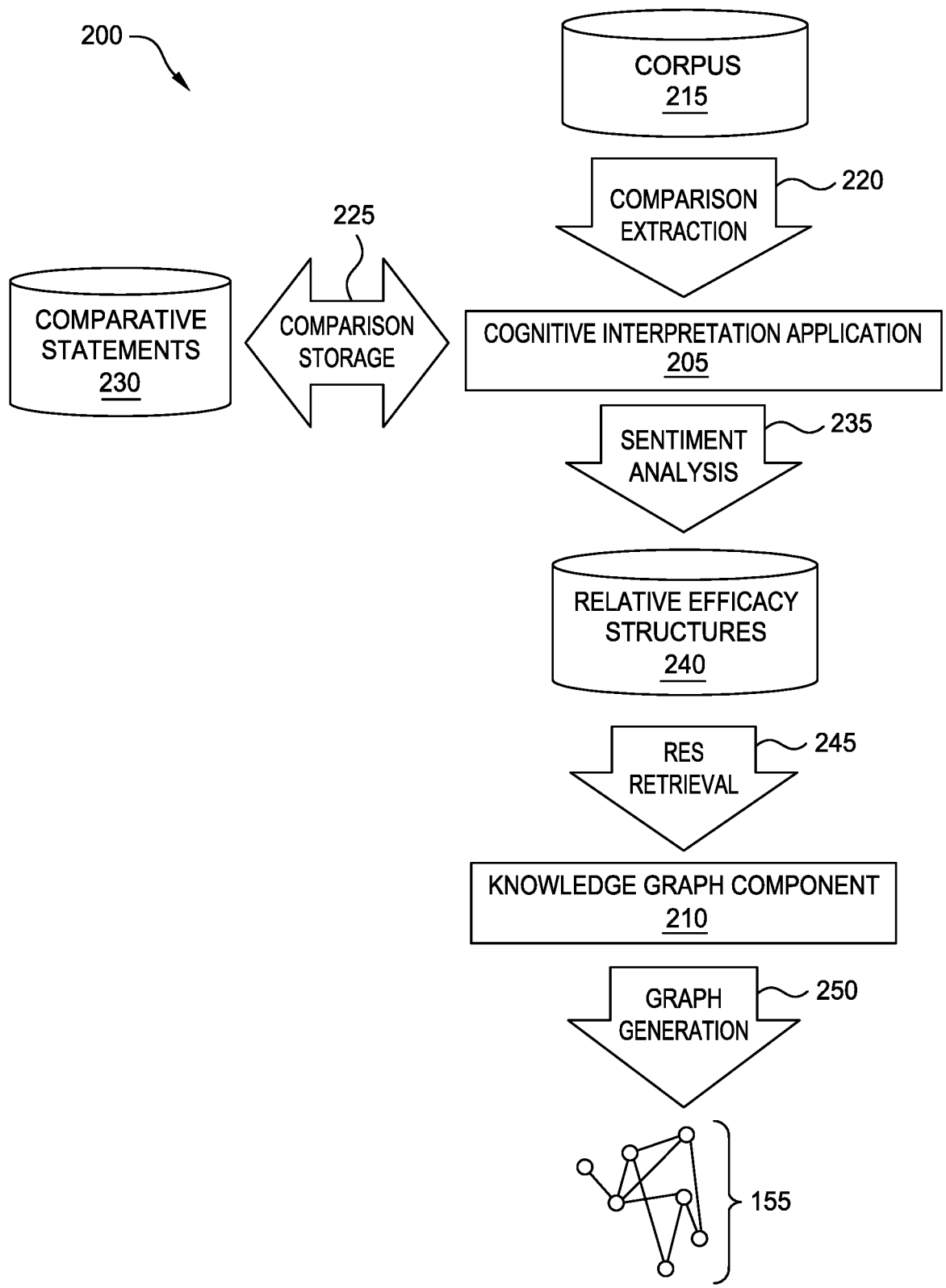
FIG. 2 illustrates a workflow for cognitively determining the relative efficacy of therapies, according to one embodiment disclosed herein.

FIG. 2 illustrates a workflow 200 for cognitively determining the relative efficacy of therapies, according to one embodiment disclosed herein. In the illustrated embodiment, a Cognitive Interpretation Application 205 analyzes documents to extract Comparative Statements 230 and generate RESs 240, and a Knowledge Graph Component 210 analyzes these RESs 240 to generate a Knowledge Graph 255. In some embodiments, a Knowledge Graph 255 is generated to aid visualization or understanding of the literature (although it may not actually be displayed). In some embodiments, however, the knowledge graph is not created, and the RESs 240 are used for other purposes. That is, in some embodiments, the generated RESs are usable or searchable by other systems or components, and can be utilized to aid understanding and improve treatment selection, without the construction of a knowledge graph.

In the illustrated workflow 200, the Cognitive Interpretation Application 205 analyzes a Corpus 215 of documents to perform Comparison Extraction 220. In an embodiment, the Corpus 215 includes documents which include at least some portion of natural language text, which may or may not have comparative statements by the author(s). In some embodiments, the Corpus 215 corresponds to a particular domain of interest to a user. For example, in one embodiment, a larger corpus or collection of documents is searched to identify a subset of the documents that relate to a particular disorder, therapy, or set of disorders or therapies. In such an embodiment, this subset of documents makes up the Corpus 215. In some embodiments, the workflow 200 is performed on multiple corpora (e.g., once for each therapy or disorder).

In an embodiment, the Comparison Extraction 220 comprises utilizing one or more natural language processing (NLP) techniques to identify comparative statements in the text included in the Corpus 215. For example, in one embodiment, the Cognitive Interpretation Application 205 searches for comparative language (such as "superior," "better," "worse," "improved," and the like). In some embodiments, the Cognitive Interpretation Application 205 analyzes predefined sections of the documents to identify these comparative statements (e.g., the abstract, conclusion, methods, discussion, etc.). That is, in an embodiment, a user or administrator can specify portions or sections in the documents that should be analyzed. In other embodiments, the Cognitive Interpretation Application 205 analyzes the full text of the document. In one embodiment, the Cognitive Interpretation Application 205 first searches the identified sections (as identified by their headings or by metadata tags), and only parses the rest of the document if the specified section(s) do not include any comparative statements (or if the specified section(s) cannot be found or do not exist in the document).

In some embodiments, the Comparison Extraction 220 also includes remedying unknown terms in the statement, such as through disambiguation and acronym resolution. For example, if the comparative statement includes an acronym, in one embodiment, the Cognitive Interpretation Application 205 can expand the acronym. Similarly, if the statement includes ambiguous or general language (such as, "all treatments studied herein", "with respect to the relevant cohort," or "generic chemotherapy drugs"), the Cognitive Interpretation Application 205 can determine a meaning for the terms. In some embodiments, the Cognitive Interpretation Application 205 first parses the selected document to identify the meaning of the term. That is, the Cognitive Interpretation Application 205 attempts to find meaning for the unknown term by analyzing the text of the document in which the comparative statement was found using NLP techniques. If no satisfactory disambiguation is found (e.g., the confidence level of any potential disambiguations is below a threshold), the Cognitive Interpretation Application 205 can access other literature (or one or more knowledge graphs) to disambiguate the term. In some embodiments, if the true meaning is not found within the corresponding document, the confidence or weight of the extracted comparison is reduced.

In some embodiments, Comparison Extraction 220 includes annotation of the extracted comparative statements. For example, in one embodiment, the Cognitive Interpretation Application 205 utilizes one or more NLP techniques to identify the therapy or therapies involved in the statement, the qualifier or comparative term utilized, and the like. In some embodiments, the Cognitive Interpretation Application 205 also determines the cohort(s) to which the statement(s) apply, as discussed in more detail below. Additionally, in some embodiments, the Cognitive Interpretation Application 205 determines characteristics of the comparative statements, such as where in the text it was located (e.g., which section it was found in), the publication date of the document, whether the document has been peer-reviewed, an identity of the publisher or entity that provided the document, and the like.

In the illustrated embodiment, the Cognitive Interpretation Application 205 stores the extracted comparisons (e.g., the natural language text) in a data store for Comparative Statements 230. In some embodiments, these stored Comparative Statements 230 are annotated to identify the relevant therapies, qualifiers, and the like. In some embodiments, the Comparative Statements 230 also indicate the disorder that is relevant to the comparison. In other embodiments, the disorder is described by the cohort and/or cohort qualifiers. In embodiments, the Comparative Statements 230 can be stored locally by the Cognitive Interpretation Application 205, or in one or more remote storage locations (such as in the cloud). As illustrated, the Cognitive Interpretation Application 205 then performs Sentiment Analysis 235 on the extracted Comparative Statements 230, to generate a set of RESs 240. In an embodiment, this Sentiment Analysis 235 includes classifying each statement as positive, negative, or neutral with respect to each of the implicated therapies. In some embodiments, the Cognitive Interpretation Application 205 also determines a degree of the sentiment (based on, for example, the strength of the language or term used). Further, in some embodiments, the RESs 240 include an indication as to which outcome or outcome type the comparison relates to (e.g., overall survival, progression-free survival, etc.).

In some embodiments, the RESs 240 include an indication as to the therapies involved, the relevant cohort, and the like. In one embodiment, each RES 240 corresponds to a particular Comparative Statement 230. In one embodiment, each RES 240 is weighted based on a variety of factors. For example, in an embodiment, the weighting factors include how recently the corresponding document was published, whether the document has been peer-reviewed, the identity of the publisher or provider for the document, the number of patients evaluated in the clinical study, and the like. In one embodiment, publishers are associated with predefined weights or strengths, based on their prestige or trustworthiness. In some embodiments, the Cognitive Interpretation Application 205 weights each RES 240 based on a confidence level as well. In one embodiment, this confidence level is based in part on a confidence value returned by the NLP models. Further, in an embodiment, the confidence is adjusted based on where in the document the corresponding Comparative Statement 230 was found. For example, a comparison found in the abstract or conclusion can be given a higher weight, while a comparison found elsewhere in the document can be given a lower weight.

In the illustrated embodiment, the Knowledge Graph Component 210 retrieves these RESs 240 from the data store, and performs Graph Generation 250 to generate a Knowledge Graph 255. In an embodiment, each node in the Knowledge Graph 255 is a therapy (or combination of therapies), and each edge is based on the determined relationships and relative efficacies (e.g., the RESs 240). In one embodiment, the Knowledge Graph Component 210 adds an edge or connection for each determined RESs 240 (e.g., for each comparative statement found). In some embodiments, the Knowledge Graph Component 210 aggregates the comparisons. For example, in an embodiment, for each outcome type and cohort combination, the Knowledge Graph Component 210 can aggregate the corresponding RESs 240, in order to determine an overall relative efficacy for the therapies, with respect to the cohort and outcome. In some embodiments, this aggregation is based in part on the weights of each comparison, as discussed above.

Although not depicted in the illustrated embodiment, in some embodiments, the Cognitive Interpretation Application 205 also identifies statements relating to the efficacy or outcomes of a therapy, even in the absence of a comparison between therapies. In such an embodiment, the Cognitive Interpretation Application 205 can also perform Sentiment Analysis 235 on the non-comparative statements to determine whether the therapy is being referred to in a positive, neutral, or negative manner. In some embodiments, the Cognitive Interpretation Application 205 also determines the efficacy and/or outcomes of the therapy, if available in the Corpus 215. For example, in such an embodiment, the Cognitive Interpretation Application 205 can determine what percentages of patients benefitted (with respect to each potential outcome), the magnitude of the benefits, and the like. In an embodiment, the Knowledge Graph Component 210 then incorporates these non-comparative statements into the Knowledge Graph 255 (e.g., by adding or refining a node corresponding to the therapy being discussed).

Figure 3:
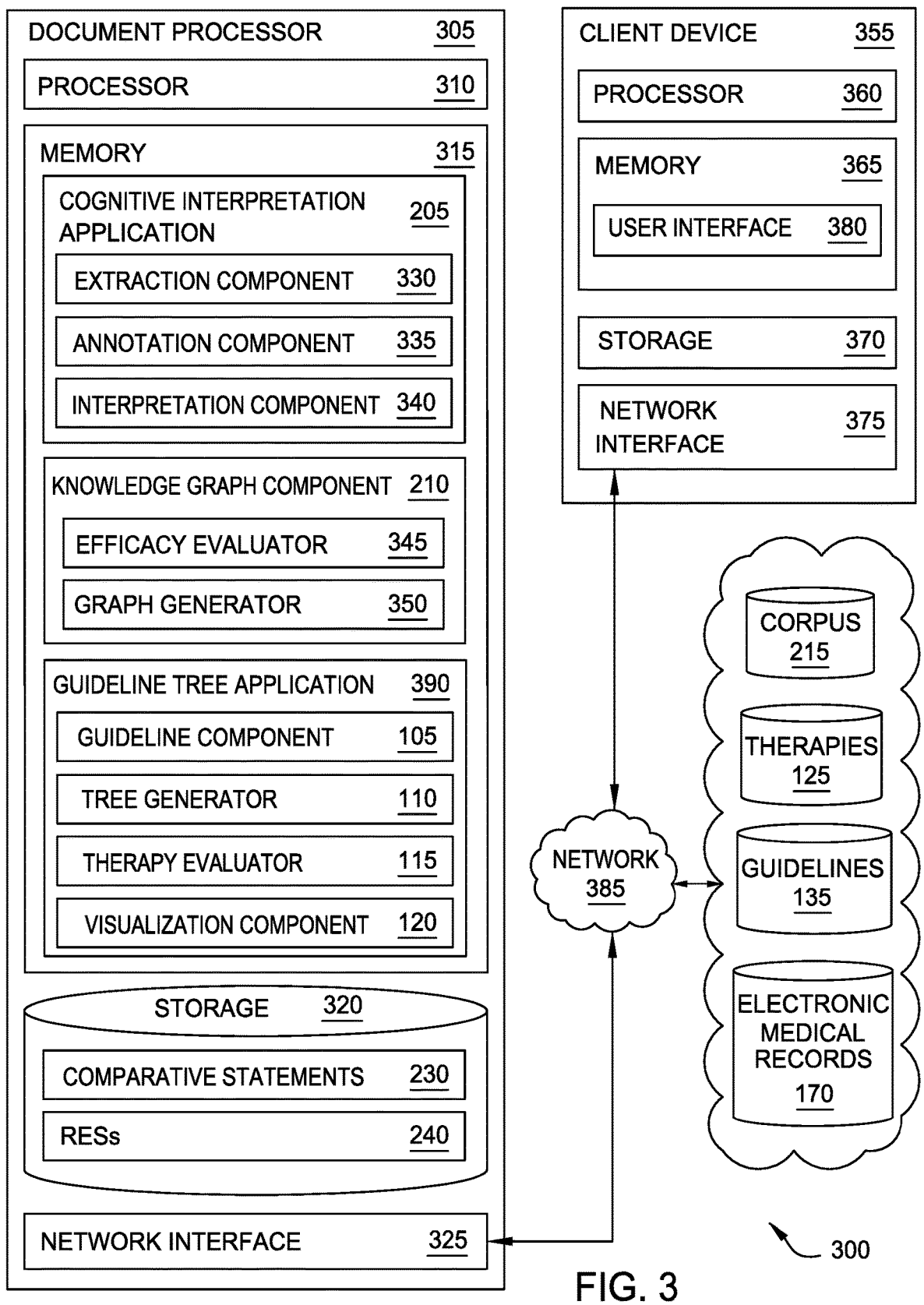
FIG. 3 is a block diagram of a system configured to generate and manipulate guideline trees, and to cognitively determine the relative efficacy of therapies, according to one embodiment disclosed herein.

FIG. 3 is a block diagram of a system 300 configured to cognitively determine the relative efficacy of therapies, according to one embodiment disclosed herein. In the illustrated embodiment, the system 300 includes a Document Processor 305, a Client Device 355, a Corpus 215, and data stores for Therapies 125, Guidelines 135, and EMRs 170. Although illustrated as discrete components, in embodiments, the Document Processor 305, Client Device 355, Corpus 215, Therapies 125, Guidelines 135, and EMRs 170 may operate or reside on a single device, or may be distributed across any number of devices. As illustrated, the Document Processor 305, Client Device 355, Corpus 215, Therapies 125, Guidelines 135, and EMRs 170 are communicatively linked through a Network 385. In one embodiment, the Network 385 is the Internet.

As illustrated, the Document Processor 305 includes a Processor 310, a Memory 315, and Storage 320. In the illustrated embodiment, Processor 310 retrieves and executes programming instructions stored in Memory 315 as well as stores and retrieves application data residing in Storage 320. Processor 310 is representative of a single CPU, multiple CPUs, a single CPU having multiple processing cores, and the like. Memory 315 is generally included to be representative of a random access memory. Storage 320 may be a disk drive or flash-based storage device, and may include fixed and/or removable storage devices, such as fixed disk drives, removable memory cards, or optical storage, network attached storage (NAS), or storage area-network (SAN). Via the Network Interface 325, the Document Processor 305 can be communicatively coupled with corpuses of documents (such as Corpus 215, Therapies 125, Guidelines 135, and EMRs 170), Client Devices 355, and the like.

In the illustrated embodiment, the Storage 320 of the Document Processor 305 includes a set of Comparative Statements 230 and RESs 240. In some embodiments, the Storage 320 also includes a Knowledge Graph 155 and/or Guideline Trees 160. In some embodiments, as discussed above, the Comparative Statements 230, and/or RESs 240 may be stored in one or more remote storage locations, such as in the cloud. Further, in some embodiments, the Storage 320 includes non-comparative statements as well. As discussed above, in an embodiment, the Comparative Statements 230 are annotated natural language text extracts from documents in the Corpus 215. In one embodiment, each Comparative Statement 230 includes a comparison or opinion of the author of the corresponding document. In some embodiments, the annotations indicate the qualifier or comparator used by the author, the therapies implicated by the statement, the cohort or cohort qualifiers that limit the applicability of the comparison, and the like. Further, in some embodiments, the Comparative Statements 230 include publication characteristics of the statements, such as the location in their corresponding documents where they were found, the date of the publication, the entity that published it, and the like. Additionally, in one embodiment, the Comparative Statements 230 include an indication as to the confidence value that the NLP model(s) generated when parsing the statements.

As discussed above, in one embodiment, each RES 240 is a data structure representing a particular Comparative Statement 230. In some embodiments, each RES 240 indicates the therapies involved, the directionality or sentiment of the comparison, the cohort implicated, and the like. Further, in an embodiment, each RES 240 includes a weight, which can be based on a variety of factors including the publication characteristics of the underlying Comparative Statement 230, the confidence of the NLP model(s), and the like. In some embodiments, the RESs 240 are configured to be searchable, such that other systems or components (such as the Knowledge Graph Component 210) can readily access the information, and obtain an up-to-date and comprehensive understanding of the current state of the literature.

In the illustrated embodiment, the Memory 315 of the Document Processor 305 includes a Cognitive Interpretation Application 205, a Knowledge Graph Component 210, and a Guideline Tree Application 390. The Cognitive Interpretation Application 205 includes an Extraction Component 330, an Annotation Component 335, and an Interpretation Component 340. Although depicted as discrete components for illustration, in embodiments, the operations and functionality of the Extraction Component 330, Annotation Component 335, and Interpretation Component 340 can be combined or divided across any number of components. Further, although depicted as software components residing in Memory 315, in embodiments, the operations and functionality of the Extraction Component 330, Annotation Component 335, and Interpretation Component 340 can be implemented using hardware, software, or a combination of hardware and software.

In an embodiment, the Extraction Component 330 identifies and extracts statements that include comparisons between therapies or treatment options from documents in the Corpus 215, as discussed above. In some embodiments, the Extraction Component 330 utilizes one or more NLP techniques or models to identify the relevant text. Further, in an embodiment, the Annotation Component 335 annotates the extracted statements. In one embodiment, the Annotation Component 335 utilizes predefined rules, and/or additional NLP models and/or techniques to annotate the statements. These annotated statements are then stored in the Comparative Statements 230. In this way, the textual comparisons found in the Corpus 215 are organized and represented in the Storage 320.

In the illustrated embodiment, the Interpretation Component 340 retrieves these Comparative Statements 230 and performs logical interpretation or sentiment analysis on them. In one embodiment, the Interpretation Component 340 classifies each Comparative Statement 230 as positive, negative, or neutral, with respect to each pair of involved therapies or treatments. For example, if the statement is that "treatment A led to better results than treatment B," the Interpretation Component 340 can determine that the comparison is positive with respect to treatment A, and negative with respect to treatment B. Similarly, if the statement is "treatments C and D were both inferior to treatment E," the Interpretation Component 340 determines that, as between therapies C and D, the sentiment is "neutral" or equal. However, as between treatment E and treatments C and D, the sentiment is positive. In this way, the Interpretation Component 340 determines the efficacy of each therapy, as compared to one or more other therapies in the statement.

In one embodiment, the Interpretation Component 340 also generates RESs 240 based on this analysis, as discussed below in more detail. That is, in an embodiment, the Interpretation Component 340 generates an organized and defined data structure that includes the relevant information from the textual Comparative Statement 230. In some embodiments, the Interpretation Component 340 generates a single RES 240 for each Comparative Statement 230. For example, in such an embodiment, if the sentiment is that treatment A is better than treatment B, the Interpretation Component 340 will generate a RES 240 indicating that treatment A is positive with respect to treatment B. In some embodiments, the Interpretation Component 340 also generates a second RES 240 indicating that treatment B is negative with respect to treatment A.

In the illustrated embodiment, the Knowledge Graph Component 210 generally retrieves the RESs 240 from Storage 320, and generates one or more knowledge graphs. As illustrated, the Knowledge Graph Component 210 includes an Efficacy Evaluator 345, and a Graph Generator 350. Although depicted as discrete components for illustration, in embodiments, the operations and functionality of the Efficacy Evaluator 345 and Graph Generator 350 can be combined or divided across any number of components. Further, although depicted as software components residing in Memory 315, in embodiments, the operations and functionality of the Efficacy Evaluator 345 and Graph Generator 350 can be implemented using hardware, software, or a combination of hardware and software. In an embodiment, the Efficacy Evaluator 345 retrieves and evaluates the RESs 240. For example, in one embodiment, the Efficacy Evaluator 345 searches for RESs 240 relating to one or more disorders or therapies that a user or administrator has selected. In other embodiments, the Efficacy Evaluator 345 retrieves and evaluates all available RESs 240. In an embodiment, the evaluation includes determining whether each RES 240 is already included in the knowledge graph.

Additionally, in some embodiments, the Efficacy Evaluator 345 aggregates the RESs 240 as appropriate, to determine an overall relative efficacy for each set of therapies. For example, in one embodiment, the Efficacy Evaluator 345 identifies RESs 240 with the same endpoints (e.g., that involve the same set of therapies) and aggregates them based on their respective weights to generate an overall relative efficacy between the therapies. In an embodiment, the Graph Generator 350 generates, inserts, and updates or refines nodes and edges in the knowledge graph, based on the evaluation provided by the Efficacy Evaluator 345. In some embodiments, the Graph Generator 350 and/or Efficacy Evaluator 345 aggregate the data by identifying all RESs 240 involving the same pair of therapies and including them in the graph, in order to capture all available evidence that compares the therapies without attempting to establish whether one is overall superior to the other.

In the illustrated embodiment, the Guideline Tree Application 390 includes a Guideline Component 105, Tree Generator 110, Therapy Evaluator 115, and Visualization Component 120. Although depicted as discrete components for illustration, in embodiments, the operations and functionality of the Guideline Component 105, Tree Generator 110, Therapy Evaluator 115, and Visualization Component 120 can be combined or divided across any number of components. Further, although depicted as software components residing in Memory 215, in embodiments, the operations and functionality of the Guideline Component 105, Tree Generator 110, Therapy Evaluator 115, and Visualization Component 120 can be implemented using hardware, software, or a combination of hardware and software.

In an embodiment, the Guideline Component 105 determines the relevant set of Therapies 125 to be used when generating a Guideline Tree 160. In one embodiment, the set of Therapies 125 are provided by a user (e.g., by the treating physician). In some embodiments, the Guideline Component 105 identifies or selects the therapies based on attributes of the index patient (such as the disorder or condition to be treated). Further, in an embodiment, the Guideline Component 105 determines any applicable guidelines or criteria for each of the identified therapies. In one embodiment, the Guideline Component 105 searches the Guidelines 135 based on the identified therapies. In an embodiment, the Guidelines 135 are curated or defined by SMEs (e.g., by standards-setting bodies or entities). In some embodiments, the Guideline Component 105 further determines or identifies criteria or guidance based on evaluating a knowledge graph.

In some embodiments, the Guideline Component 105 analyzes EMRs 170 to identify attributes which should be included in the Guideline Tree 160, even if they are not included in any Guidelines 135. For example, in one embodiment, the Guideline Component 105 can use an unsupervised or semi-supervised machine learning model to discover additional relevant attributes that affect therapy decisions and/or the resulting outcomes. In an embodiment, the Guideline Component 105 parses EMRs 170 to identify, for each of one or more patients, attributes of the patient, the therapy selected to treat the patient, and the outcome(s) experienced by the patient. The Guideline Component 105 can then cluster the therapies, attributes, and/or outcomes and identify attributes that affect the decisions, using the machine learning models. For example, suppose the Guideline Component 105 determines that the proximity of the patient's home to the hospital has affects how likely the treating physician is to recommend chemotherapy, or how effective the chemotherapy is. In such an embodiment, the Guideline Component 105 can include proximity as an additional criterion or attribute to be considered for therapies involving chemotherapy, such that one or more nodes and/or edges in the generated Guideline Tree 160 reflect these discovered attributes.

In the illustrated embodiment, the Tree Generator 110 receives these identified therapies and guidelines/criteria, and generates a Guideline Tree 160, as discussed in more detail below. In an embodiment, each leaf in the Guideline Tree 160 corresponds to one of the indicated therapies, and the edges and internal nodes in the Guideline Tree 160 are generated and linked based on the indicated guidelines and/or criteria. In an embodiment, the Visualization Component 120 can then generate a visual representation of the Guideline Tree 160. In some embodiments, the visualization is generated and displayed locally on the Client Device 355. Further, in the illustrated embodiment, the Therapy Evaluator 115 can analyze the knowledge graph and/or EMRs to evaluate the indicated therapies, in order to determine an optimal or recommended therapy. In some embodiments, the Visualization Component 120 can modify the Guideline Tree 160 (or modify the generated visualization) based on these evaluations, as discussed below in more detail.

In the illustrated embodiment, the Client Device 355 includes a Processor 360, a Memory 365, and Storage 370. In the illustrated embodiment, Processor 360 retrieves and executes programming instructions stored in Memory 365 as well as stores and retrieves application data residing in Storage 370. Processor 360 is representative of a single CPU, multiple CPUs, a single CPU having multiple processing cores, and the like. Memory 365 is generally included to be representative of a random access memory. Storage 370 may be a disk drive or flash-based storage device, and may include fixed and/or removable storage devices, such as fixed disk drives, removable memory cards, or optical storage, network attached storage (NAS), or storage area-network (SAN). Via the Network Interface 375, the Client Device 355 can be communicatively coupled with corpuses of documents (such as Corpus 215, Therapies 125, Guidelines 135, and EMRs 170), Document Processor 305, and the like.

As illustrated, the Memory 365 of the Client Device 355 includes a User Interface 380 for interacting with the Corpus 215 and/or Document Processor 305. In an embodiment, the User Interface 380 includes a graphical user interface (GUI) that lets users or administrators retrieve and review documents in the Corpus 215, Therapies 125, Guidelines 135, and EMRs 170. In some embodiments, the User Interface 380 also allows the user to select a subset of the Corpus 215, Therapies 125, Guidelines 135, and/or EMRs 170 (e.g., via search queries) to be processed by the Document Processor 305.

Although not illustrated, in embodiments, the Cognitive Interpretation Application 205, Knowledge Graph Component 210, and Guideline Tree Application 390 each provide one or more application programming interfaces (APIs) that allow the user (through the User Interface 380) to control the operations of the components. For example, in an embodiment, the user can use the User Interface 380 and APIs to indicate the set of documents to be analyzed, and to adjust any settings or configurations of the Cognitive Interpretation Application 205. Further, in an embodiment, the User Interface 380 and APIs enable the user to review the Comparative Statements 230 and/or RESs 240. Additionally, in an embodiment, the User Interface 380 and APIs allow the user to direct the Knowledge Graph Component 210 to generate one or more knowledge graphs based on the RESs 240, and to analyze and parse the generated graphs. Additionally, in an embodiment, the APIs associated with the Guideline Tree Application 390 allow the user to generate and visualize Guideline Trees 160.

Figure 4A:
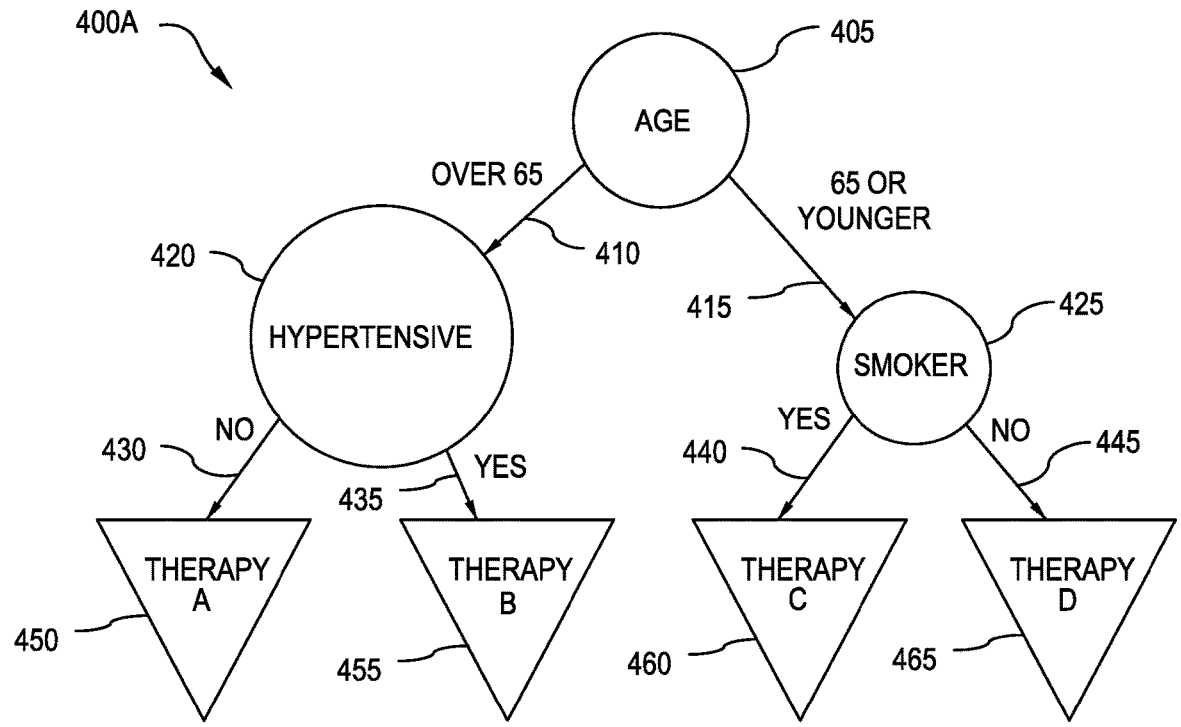
FIGS. 4A-4D illustrate visualizations for guideline trees based on patient attributes and optimal treatments, according to one embodiment disclosed herein.

FIG. 4A illustrates a Visualization 400A for guideline trees based on patient attributes and optimal treatments, according to one embodiment disclosed herein. As illustrated in FIGS. 4A, Visualization 400A is provided for a guideline tree having four therapies. In the illustrated Visualization 400A, the corresponding tree is a binary tree (e.g., each node has exactly two children nodes). Of course, in embodiments, the tree need not be binary, and each node may have any number of edges/children. Additionally, the leaves of the tree need not be at the same level (e.g., a first leaf node and a second leaf node may have a differing number of edges that must be traversed to connect to the root node). In the illustrated embodiment, the root Node 405 corresponds to the age of the patient. That is, the first attribute to be considered when evaluating the patient against the guideline tree is the age of the patient.

As illustrated, if the index patient is "over 65" in age, the workflow passes to the Node 420. If the patient is "65 or younger," the workflow continues to the Node 425. In the illustrated embodiment, the attribute associated with the Node 420 is hypertension. Specifically, as illustrated, if the patient is not hypertensive, the suggested therapy is Therapy A, corresponding to leaf Node 450, as illustrated by the Edge 430. In contrast, if the patient is hypertensive, the guidelines suggest Therapy B, included in leaf Node 455, as illustrated by Edge 435. Thus, in the illustrated embodiment, if the index patient is over 65, whether Therapy A or Therapy B is recommended by the Guidelines 135 depends on whether the patient is hypertensive or not.

In the illustrated embodiment, the Node 425 corresponds to tobacco use. Specifically, as illustrated by the Edge 440, if the patient uses tobacco, the appropriate treatment is Therapy C (corresponding to leaf Node 460). In contrast, if the patient does not use tobacco, Therapy D (included in leaf Node 465) is the suggested treatment (as illustrated by Edge 445). Thus, as illustrated, if the patient is 65 or younger, whether Therapy C or Therapy D is appropriate turns on whether the patient consumes tobacco. In embodiments, a given leaf node (corresponding to a particular therapy) may have multiple parent nodes. For example, suppose the guidelines indicate that Therapy C is best for patients who are 65 or younger that also smoke, OR for patients 65 and older who are hypertensive. In such an embodiment, the leaf Node 460 would be linked to both the Node 425 and Node 420. Further, in an embodiment, depending on the particular guidelines, a given edge may link to a collection or set of therapies, rather than a single therapy (e.g., indicating that any therapy in the set is acceptable or suggested, based on the existing guidelines). Further, in some embodiments, a given attribute may be associated with multiple nodes. For example, whether a patient consumes tobacco may be a relevant factor at multiple points in the tree, depending on the particular guidelines.

Figure 4B:
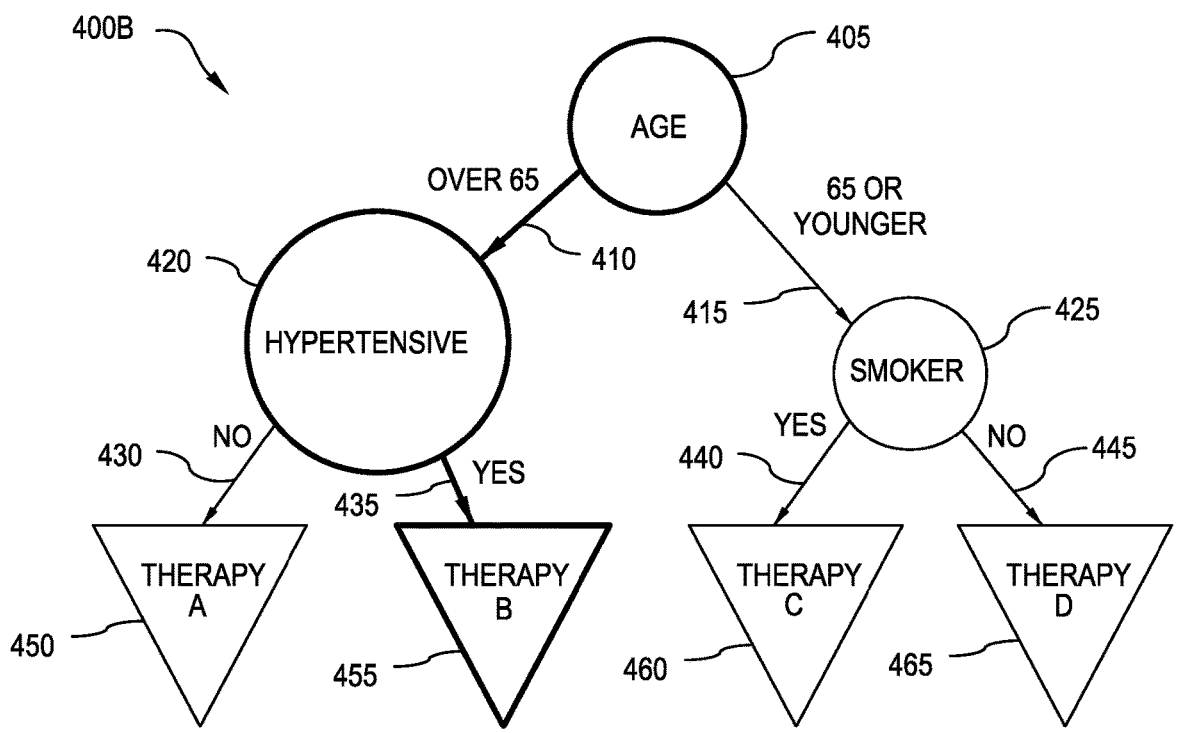

FIG. 4B illustrates a Visualization 400B for guideline trees based on patient attributes and optimal treatments, according to one embodiment disclosed herein. In the illustrated Visualization 400B, the display (or the guideline tree itself) has been modified based on the attributes of an index patient. In particular, as illustrated, the index patient is over 65, and is hypertensive. Thus, based on the guidelines represented by the tree, Therapy B is the suggested treatment. Further, as illustrated, the Visualization Component 120 has emphasized the Node 455 to indicate that the Therapy B is suggested. Further, as illustrated, the Visualization Component 120 emphasized the Nodes 420 and 405, as well as Edges 410 and 435, to indicate the path through the guideline tree that is associated with the patient attributes.

In embodiments, the Visualization Component 120 can utilize any technique to emphasize the therapy and/or path. For example, the Visualization Component 120 may highlight the path and leaf node, change the color(s) of the determined path and nodes, make the path bold, and the like. In some embodiments, the Visualization Component 120 can also increase the size of the relevant path, decrease the size of the other edges and nodes, adjust the opacity of the path and/or the other nodes and edges outside of the path, and the like. In this way, the user can quickly ascertain the appropriate therapy, as well as how the patient's attributes map to the guideline tree. In particular, the user can readily perceive why suggested therapy was indicated, and which nodes and attributes were key.

Figure 4C:
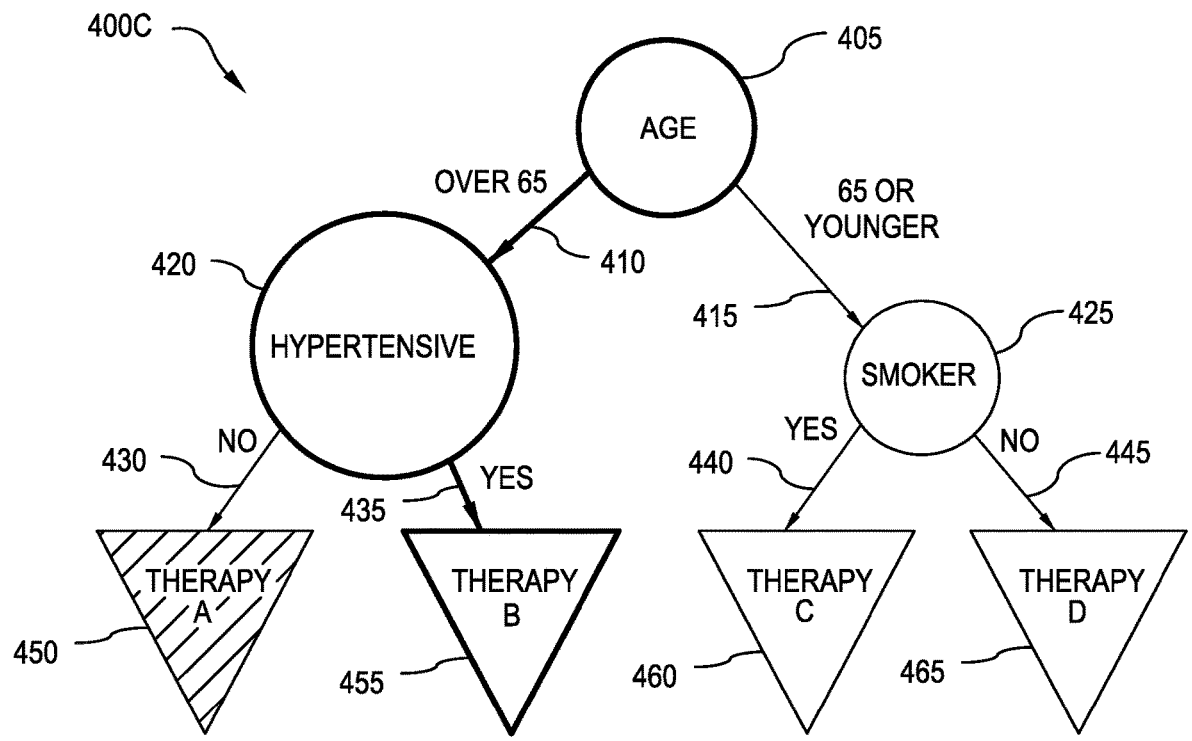

FIG. 4C illustrates a Visualization 400C for guideline trees based on patient attributes and optimal treatments, according to one embodiment disclosed herein. In the illustrated Visualization 400C, the display (or the guideline tree itself) has been modified based on a determined optimal or preferred therapy. In particular, as illustrated, the Therapy Evaluator 115 has determined that the Therapy A is preferred and/or optimal for the index patient, based on evaluating a knowledge graph and/or EMRs. For example, in one embodiment, the Therapy Evaluator 115 may analyze the knowledge graph to determine that the Therapy A is superior based on the current published literature (e.g., based on clinical trials and studies) which may not have been incorporated in the guidelines. Additionally, in an embodiment, even though the patient does not align with the guidelines for the Therapy A, the Therapy Evaluator 115 may determine (based on the knowledge graph) that the Therapy A is still likely to be the superior therapy.

Similarly, in an embodiment, the Therapy Evaluator 115 analyzes EMRs associated with other patients in the same cohort as the index patient, in order to determine which therapy each patient received, and what the outcome was for the patient. In this way, the Therapy Evaluator 115 can determine whether a particular therapy tends to have better outcomes, based on real world evidence. In the illustrated embodiment, based on determining that the Therapy A is preferred, superior, or optimal, the Visualization Component 120 has emphasized the corresponding leaf Node 450. In the illustrated embodiment, this emphasis includes changing the color or shading of the node. Of course, in embodiments, this visualization can differ based on the particular implementation, and can include highlighting the node, changing its color, changing its size, and the like.

Figure 4D:
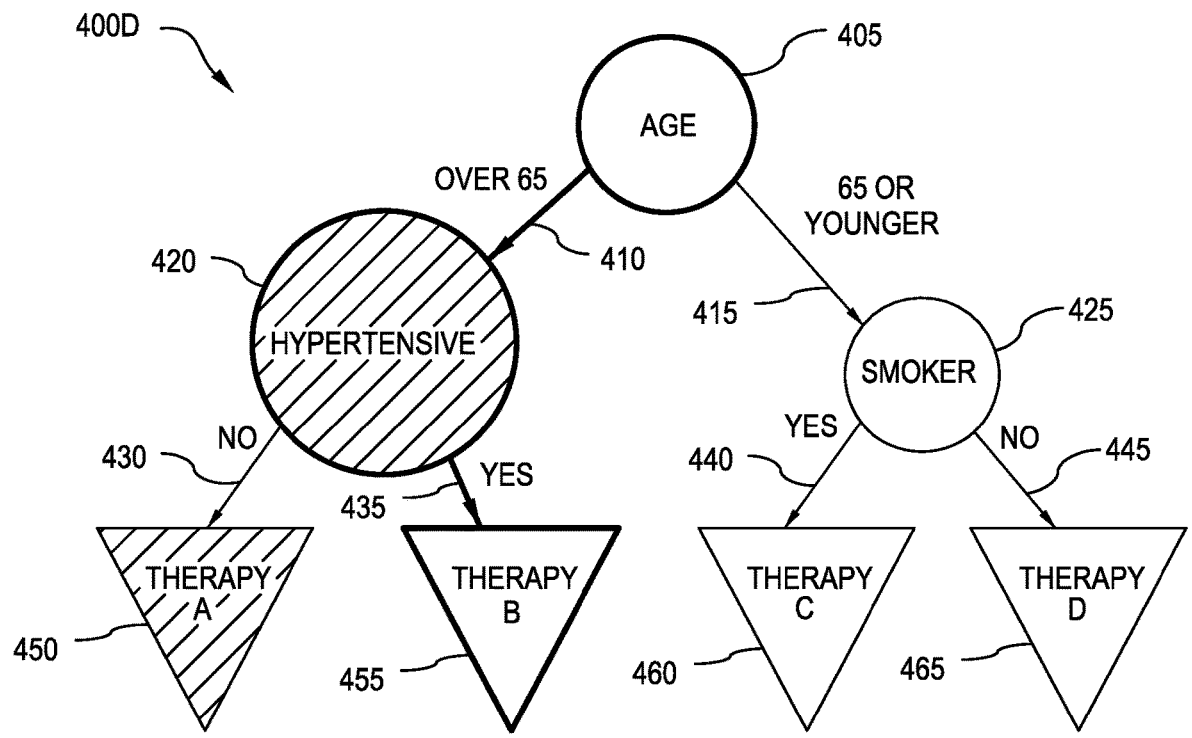

FIG. 4D illustrates a Visualization 400D for guideline trees based on patient attributes and optimal treatments, according to one embodiment disclosed herein. In the illustrated embodiment, the display has been modified to indicate the key node in the guideline tree where the index patient attributes caused the suggested therapy to differ from the determined optimal or preferred therapy. That is, in the illustrated embodiment, the Visualization Component 120 determines the path from the root node to the leaf node for the suggested therapy (e.g., Therapy B) as indicated by the guidelines. The Visualization Component 120 further determines the path from the root to the leaf node corresponding to the optimal therapy (Therapy A). In the illustrated embodiment, the Visualization Component 120 further identifies the node where the paths diverge. In one embodiment, if the paths diverge, converge to overlap again, and finally diverge again, the Visualization Component 120 determines the final divergence (e.g., the divergence closest to the leaf nodes).

In the illustrated embodiment, the divergent node is Node 420. By emphasizing this node, the Visualization Component 120 allows the user to quickly determine the differences between the suggested therapy and the optimal therapy, with respect to the existing guidelines. Further, the user can quickly determine how much the therapies differ, based on how far apart the ultimate leaf nodes are (or how far up the tree the divergence occurred). Additionally, because the associated attribute is hypertension, the user can quickly determine that if the patient's attributes with respect to hypertension can be changed, the suggested therapy may change as well.

In some embodiments, in addition to identifying the divergent node, the Visualization Component 120 can provide an indication of the relevant attribute. In one embodiment, the Visualization Component 120 can also indicate whether the attribute is mutable, such that the patient might be able to change their attributes to comply with the guidelines for the optimal therapy. In this way, the Visualization Component 120 can present dynamic visualizations that enable healthcare providers to easily perceive how a patient's attributes align with the criteria and guidelines, and which attributes are driving the suggested therapy. Of course, although the illustrated guideline tree is relatively simple, in embodiments, the guideline tree may be significantly more complex, and can include any number of nodes and edges. In these more complex trees, the visualization becomes particularly important, in order to illustrate how and why the patient's suggested therapy differs from optimal therapies.

In some embodiments, the visualizations can be modified to illustrate how a patient's attributes (and the corresponding suggested therapy) have changed over time. For example, the path through the guideline tree at various points in time can be emphasized in different ways. In some embodiments, the tree is animated to visualize how the path has shifted and moved over time, based on the patient attributes. In some embodiments, the visualization can also be modified to illustrate how the guidelines have changed over time. For example, the guideline trees at various points in time may be animated with a morph or transformation from one tree to the next, which illustrates how the guidelines have shifted and why the suggested therapy at any given time may have differed.

Figure 5:
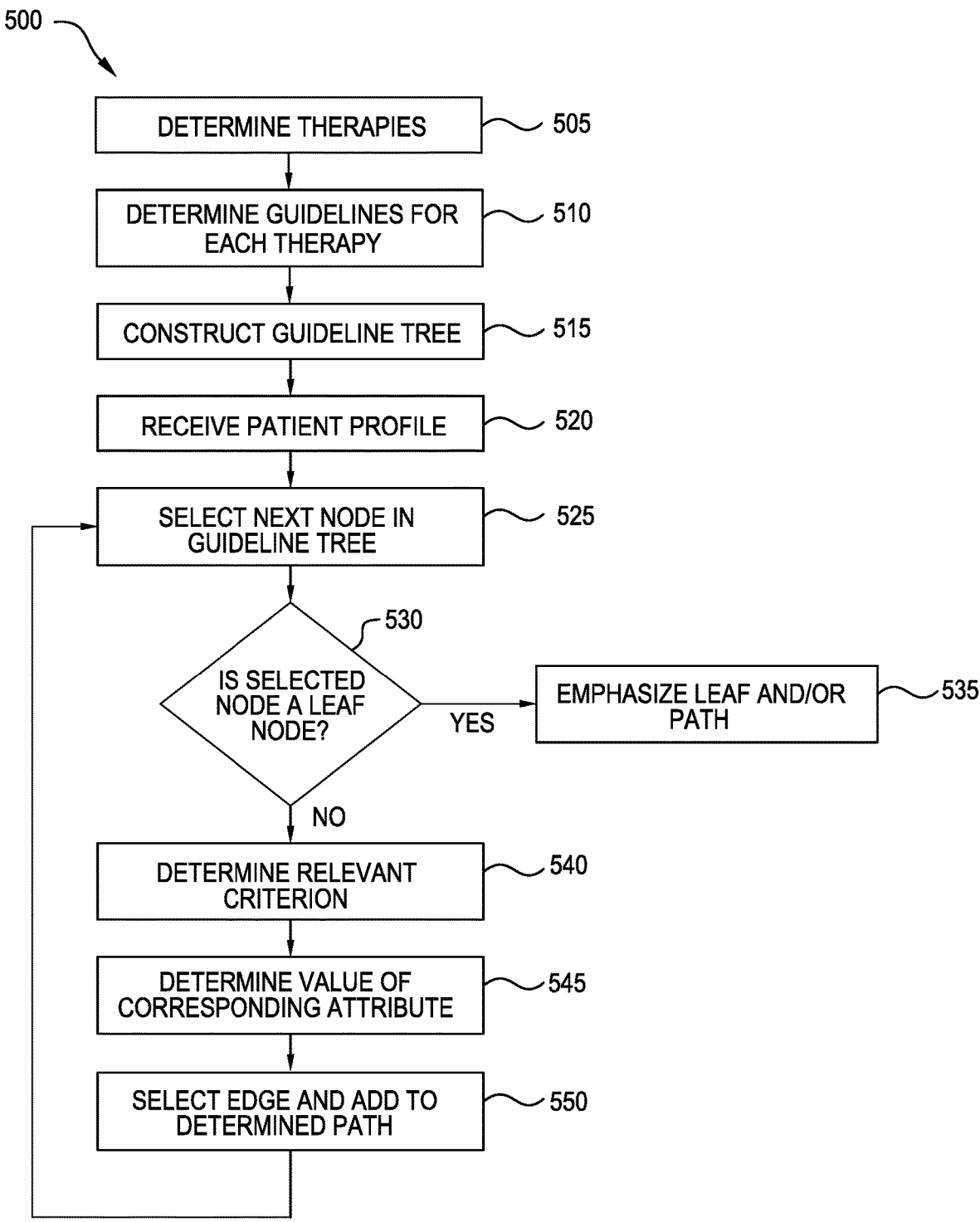
FIG. 5 is a flow diagram illustrating a method for building and using a guideline tree, according to one embodiment disclosed herein.

FIG. 5 is a flow diagram illustrating a method 500 for building and using a guideline tree, according to one embodiment disclosed herein. The method 500 begins at block 505, where the Guideline Tree Application 390 determines the therapies that should be used to construct the guideline tree. In one embodiment, this includes receiving an indication of the appropriate therapies from a user. In some embodiments, the therapies are identified based on the relevant disorder or condition, and a separate guideline tree is generated for each. The method 500 then continues to block 510, where the Guideline Tree Application 390 determines, for each of the identified therapies, a set of corresponding guidelines. In one embodiment, this includes retrieving a predefined set of guidelines that correspond to each treatment (e.g., as defined by one or more SMEs). In some embodiments, the Guideline Tree Application 390 also analyzes EMRs (e.g., using an unsupervised machine learning model) to identify attributes that affect therapy decisions.

The method 500 then proceeds to block 515, where the Guideline Tree Application 390 generates the guideline tree based on the determined therapies and guidelines. In an embodiment, each leaf node in the guideline tree corresponds to a therapy, and each edge corresponds to a guideline associated one or more therapies. Thus, in an embodiment, for a path from the root to the leaf node associated with a particular therapy, each edge in the path corresponds to a guideline that is associated with the particular therapy. In some embodiments, the guideline tree is generated based in part on an ordering of the criteria or guidelines for each therapy. For example, in one embodiment, the guidelines for a set of therapies can indicate that the first consideration is whether the patient has diabetes, followed by the age of the patient, and so on. In such an embodiment, a node associated with the status of the patient with respect to diabetes may be relatively higher in the tree (e.g., close to the root) than a node associated with age.

In some embodiments, as discussed above, the branches of the tree may diverge and converge at a subsequent node, depending on the particular guidelines. Similarly, in some embodiments, a particular attribute may be considered at multiple nodes (e.g., on different branches of the tree) and at different times, depending on the underlying guidelines. In an embodiment, to generate the guideline tree, the Guideline Tree Application 390 creates a leaf node for each potential therapy. The Guideline Tree Application 390 can then generate and insert any number of internal nodes and edges based on the individual guidelines, in order to complete the guideline tree.

The method 500 then proceeds to block 520, where the Guideline Tree Application 390 receives a patient profile for the index patient. In embodiments, the Guideline Tree Application 390 can receive an indication of a profile and determine the corresponding attributes (e.g., by analyzing one or more records associated with the indicated patient), or can receive one or more attributes themselves. In one embodiment, the healthcare provider and/or patient can input values for one or more attributes, to be used to generate a dynamic visualization of the guideline tree. The method 500 then continues to block 525 where the Guideline Tree Application 390 begins parsing the tree to identify the suggested therapy by selecting the next node in the guideline tree. Specifically, the first node to be considered (e.g., the "next node" when no other nodes have been considered) is the root node of the tree. The method 500 then continues to block 530.

At block 530, the Guideline Tree Application 390 determines whether the selected node is a leaf in the tree. That is, the Guideline Tree Application 390 determines whether the node corresponds to a particular therapy, or if it is an internal node associated with one or more attributes. If the node is a leaf node, the method 500 proceeds to block 535, where the Guideline Tree Application 390 determines that the corresponding therapy is the suggested therapy (based on the existing guidelines), and emphasizes the selected node (e.g., by highlighting it, changing its color, and the like). In some embodiments, the Guideline Tree Application 390 further highlights or emphasizes the path in the guideline tree leading from the root node, through one or more nodes and/or edges, to the leaf node. The method 500 then terminates.

Returning to block 530, if the Guideline Tree Application 390 determines that the selected node is not a leaf node, the method 500 proceeds to block 540, where the Guideline Tree Application 390 determines the relevant attribute or criterion for the selected node. In one embodiment, the node itself indicates the relevant criterion. In some embodiments, the Guideline Tree Application 390 analyzes a label attached to each edge below the node in order to determine the corresponding criteria. For example, in embodiments, the node may specify that "age" is the relevant attribute, or the Guideline Tree Application 390 can determine that age is the relevant attribute based on determining that the edges leaving the node are use age as the determining factor.

Once the criterion is determined, the method 500 continues to block 545, where the Guideline Tree Application 390 determines a value of the corresponding attribute, with respect to the index patient (e.g., based on the patient profile). For example, if the relevant attribute is whether the patient's cancer has metastasized, the Guideline Tree Application 390 can determine whether the index patient's cancer has metastasized, or can determine a stage of the patient's cancer. In one embodiment, if the patient profile does not specify a value for the attribute (or a value for the attribute cannot be determined based on EMRs associated with the patient), the Guideline Tree Application 390 can prompt the user or patient to enter a value.

The method 500 then continues to block 550, where the Guideline Tree Application 390 selects the next edge, and adds this selected edge (and, in some embodiments, the current node) to the determined path associated with the index patient. In an embodiment, the Guideline Tree Application 390 selects the appropriate edge based on determining which edge aligns with the determined attribute value. The method 500 then returns to block 525, to select the next node. In some embodiments, depending on the particular guidelines and attributes of the index patient, it may be possible that there is no suggested therapy for the index patient. For example, suppose the patient's attributes yield a path through the guideline tree that leads to a node that is not a leaf node (e.g., there is at least one node beneath it), but where there is no appropriate edge. For example, suppose the node corresponds to "body mass index," and no edges from the node correspond to a body mass index of greater than 30. If the patient's BMI is greater than 30, there will be no therapy to suggest, as the patient does not align with any of the existing therapies. In one embodiment, the Guideline Tree Application 390 can emphasize this node, and indicate that the patient's BMI is too high for any of the potential therapies.

Figure 6:
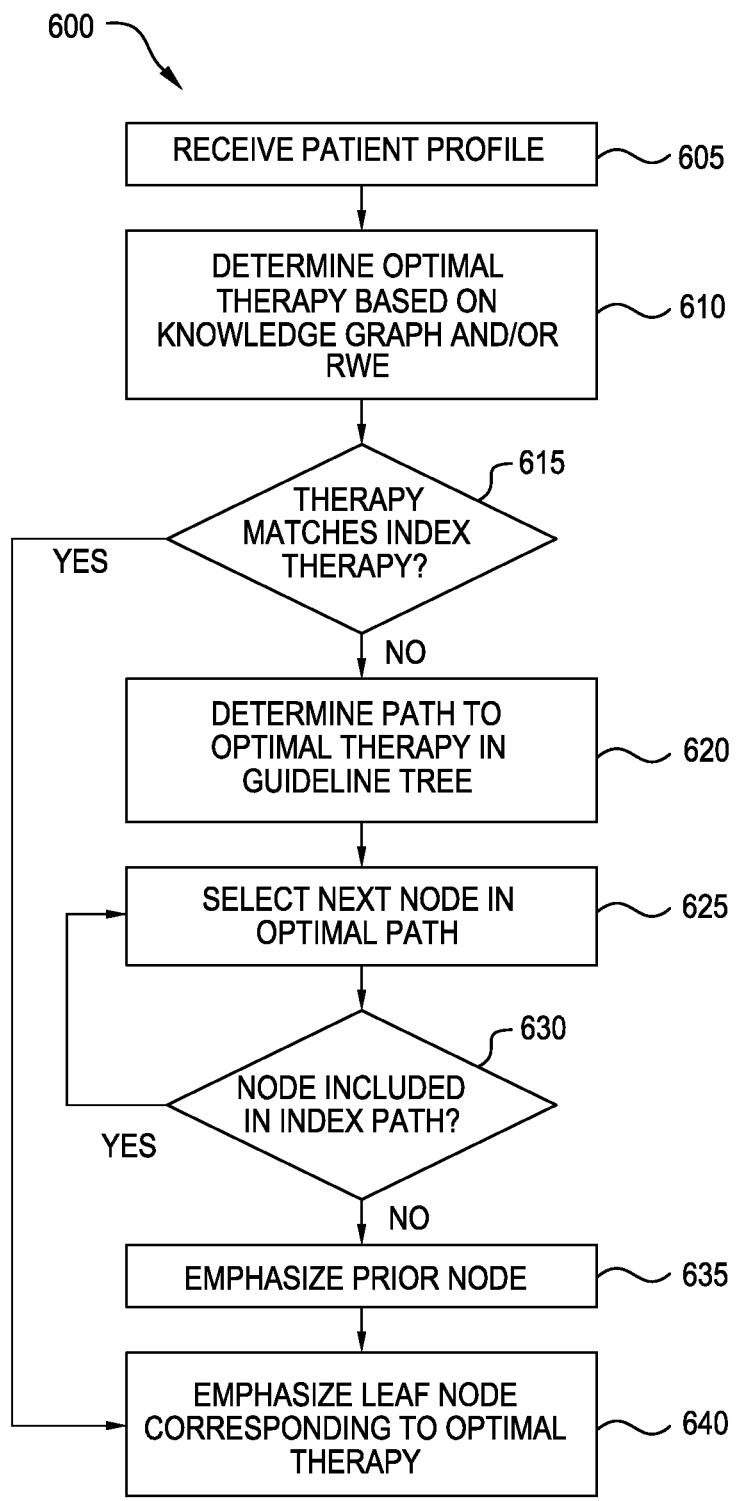
FIG. 6 is a flow diagram illustrating a method for using a guideline tree to visualize therapies, according to one embodiment disclosed herein.

FIG. 6 is a flow diagram illustrating a method 600 for using a guideline tree to visualize therapies, according to one embodiment disclosed herein. The method 600 begins at block 605, where the Guideline Tree Application 390 receives a patient profile. As discussed above, in some embodiments, this can include receiving an indication of a profile, or receive the profile itself, where the profile specifies one or more attributes of a patient. Further, in embodiments, this can include receiving one or more attributes directly (e.g., entered by a user and/or by the patient). The method 600 then proceeds to block 605, where the Guideline Tree Application 390 determines an optimal therapy for the patient based on a knowledge graph and/or RWE.

In one embodiment, to identify the optimal therapy based on information contained in a knowledge graph, the Guideline Tree Application 390 can determine the relative efficacies between each therapy that is relevant to the condition being treated. In one embodiment, this includes determining the strength of each edge in the knowledge graph, based in part on the cohort or attributes of the index patient (e.g., based on how closely the index patient's attributes align with the study or trial that was analyzed to create or refine the edge). In an embodiment, for each relevant therapy, the directionality and strength of the corresponding edges in the knowledge graph are aggregated to determine an overall score for the therapy. In this way, the Guideline Tree Application 390 can determine an optimal therapy, based on predicted efficacy, using information obtained from published literature.

In one embodiment, to identify the optimal therapy based on RWE, the Guideline Tree Application 390 first identifies a set of patients who are similar to the index patient, based on their respective attributes. In one embodiment, determining the similar patients includes identifying the cohort of the index patient. In some embodiments, the cohorts are predefined. For example, in an embodiment, when evaluating cancer patients, the cohorts can be stratified by stage (e.g., stage I, stage II, stage III, and stage IV). The Guideline Tree Application 390 can then retrieve and analyze EMRs associated with one or more of these similar patients. In particular, the Guideline Tree Application 390 can analyze the EMRs to identify which therapy was prescribed, and what the outcome was for the patient. In an embodiment, the Guideline Tree Application 390 can then aggregate the data to generate a score for each therapy, based on which therapies are preferred by healthcare providers. In some embodiments, the score is further based on the outcomes experienced by each patient. In one embodiment, the score is also affected based on the similarity between the historic patient and the current patient (e.g., based on their respective attributes).

In one embodiment, the Guideline Tree Application 390 determines both the optimal therapy based on published literature (e.g., based on the knowledge graph), as well as a preferred therapy based on RWE (e.g., based on the EMRs). In some embodiments, the Guideline Tree Application 390 aggregates these scores from each body of evidence to determine an overall superior therapy. In one embodiment, the user can indicate whether they prefer that the superior therapy be identified through published literature, RWE, or a combination of the two. The method 600 then proceeds to block 615.

At block 615, the Guideline Tree Application 390 determines whether the determined optimal therapy aligns with the determined suggested therapy (e.g., the therapy that was selected based on the guidelines in the tree). That is, the Guideline Tree Application 390 determines whether the guideline-based therapy is also the determined optimal therapy. If so, the method 600 proceeds to block 640, where the Guideline Tree Application 390 emphasizes the leaf node corresponding to this therapy. In some embodiments, the Guideline Tree Application 390 also emphasizes the path leading to the therapy. If the determined optimal therapy is not the same as the therapy identified based on the guidelines, the method 600 proceeds to block 620.

At block 620, the Guideline Tree Application 390 determines the path from the root node to the determined optimal therapy. That is, the Guideline Tree Application 390 determines a set of nodes and/or edges that connect the leaf node associated with the identified optimal therapy to the root of the tree. In an embodiment, this path to the optimal therapy is referred to as the "optimal path." Similarly, in an embodiment, the path associated with the suggested therapy identified based on the guidelines in the tree is referred to as the "index path." The method 600 then continues to block 625, where the Guideline Tree Application 390 selects a next node in the optimal path. In an embodiment, as discussed above, the first node is the root node. At block 630, the Guideline Tree Application 390 determines whether the selected node is included within the index path. If so, the method 600 returns to block 625. That is, because the paths still overlap, the Guideline Tree Application 390 moves on to the next node in the optimal math in order to determine where the paths diverge.

If, at block 630, the Guideline Tree Application 390 determines that the selected node is not in the index path, the method 600 proceeds to block 635, where the Guideline Tree Application 390 emphasizes the prior node. That is, because the current node is not in the index path, the Guideline Tree Application 390 can determine that the immediately prior node is the point where the optimal path diverged from the index path. Thus, the attribute associated with the prior node may be the key factor in determining whether the patient can receive the optimal therapy. The method 600 then proceeds to block 640, discussed above. In an embodiment, as discussed above, emphasizing nodes and/or edges in the tree may include modifying the visualization to highlight the nodes or edges, change their colors, change their relative opacity compared to other nodes and edges, change their relative size, and the like.

In some embodiments, rather than beginning at the root and proceeding towards the leaves, the Guideline Tree Application 390 begins at the leaf node corresponding to either the optimal therapy or the index therapy (e.g., the therapy selected based on the guidelines alone) and works towards the root. For example, in such an embodiment, the Guideline Tree Application 390 can iteratively select the immediately prior node, and determine whether the selected node is also in the other path. That is, if the Guideline Tree Application 390 begins at the optimal therapy, it is determined whether the node is also included in the index path. In contrast, if the Guideline Tree Application 390 begins at the index therapy, it is determined whether the selected node is also in the optimal path. In this way, when the first shared node is found, the Guideline Tree Application 390 can indicate it as the last node where the paths overlapped (and thus, the node where the paths ultimately diverge).

Thus, in embodiments, the Guideline Tree Application 390 can modify the visualization to allow users to readily perceive how closely related the therapies are, as well as where the decision-making paths diverge. This can inform the healthcare provider as to how to proceed. For example, in one embodiment, the Guideline Tree Application 390 can provide an indication of the attribute that caused the differing results, and the user can determine whether this attribute can (or should) be modified. In such an embodiment, the user may suggest that the patient take certain steps in order to align themselves with the guidelines for the optimal therapy. In one embodiment, the Guideline Tree Application 390 can identify those steps (e.g., which therapies or medications may be useful to change the attribute) and indicate them to the user for consideration.

Figure 7A:
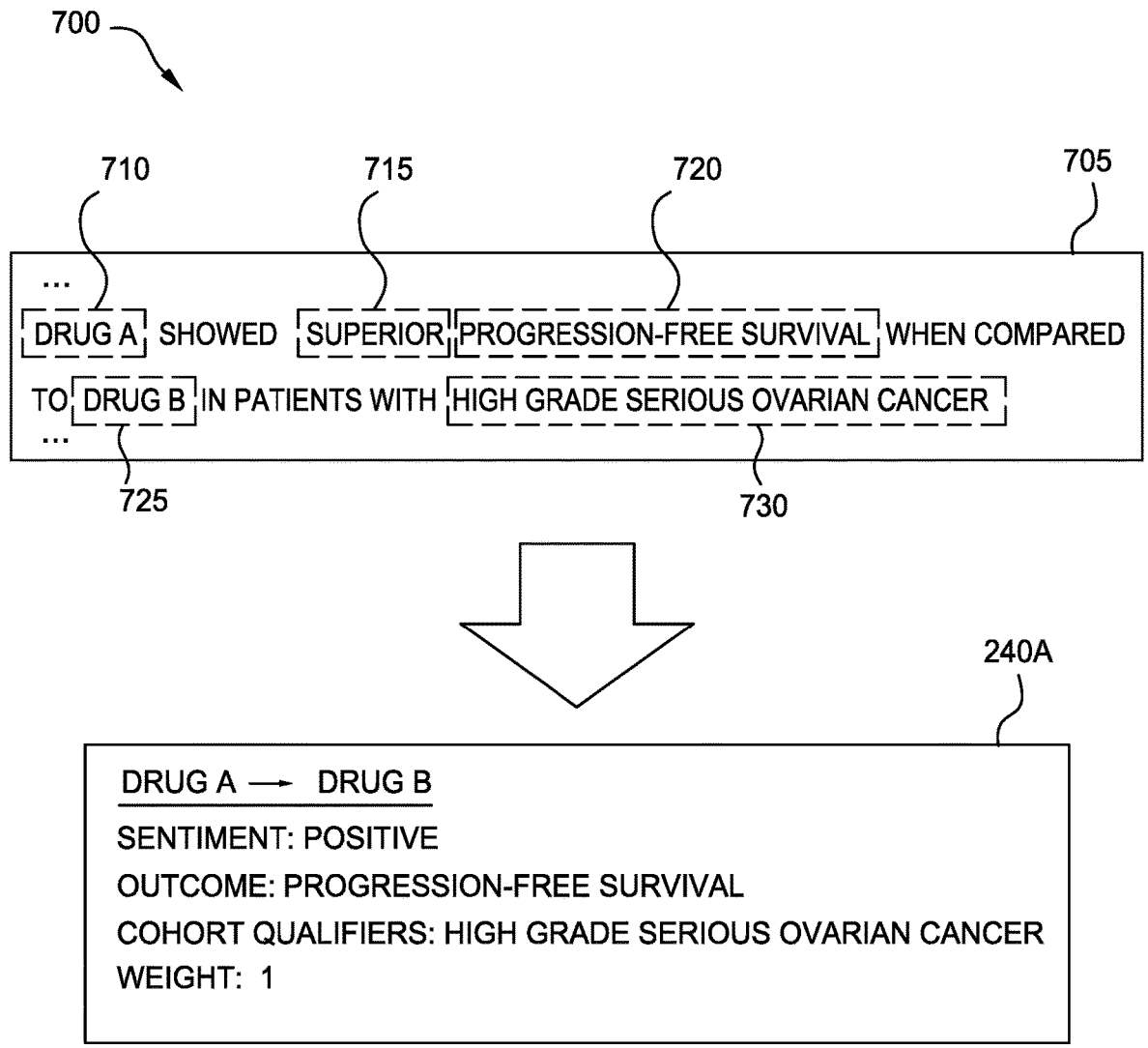
FIGS. 7A and 7B illustrate workflows for determining the efficacy for a therapy, as compared to a different therapy, according to one embodiment disclosed herein.

FIG. 7A illustrates a workflow 700 for determining the efficacy for a therapy, as compared to a different therapy, according to one embodiment disclosed herein. In the illustrated workflow 700, a comparative statement (included in an Excerpt 705) is annotated with Annotations 710, 715, 720, 725, and 730. As illustrated by the ellipses above and below the comparative statement, the original document can be any size or length. In an embodiment, the Excerpt 705 was extracted from a document (e.g., by the Extraction Component 330) based on determining that it included a comparative statement.

In the illustrated embodiment, the Excerpt 705 was annotated by the Annotation Component 335, using one or more NLP techniques. As illustrated, Annotations 710 and 725 indicate the therapies mentioned or implicated by the statement. In one embodiment, these therapies are identified based on identifying the subject and object of the statement. Further, as illustrated, the Annotation 720 indicates the outcome (also referred to as the type) that is relevant to the statement. That is, in the illustrated embodiment, the Excerpt 705 discusses the relative efficacy of Drug A and Drug B, with respect to progression-free survival. Additionally, the Annotation 715 indicates the comparator (also referred to as qualifier or type qualifier), which indicates the comparison or statement being made (e.g., that the outcome, progression-free survival, was "superior."). Finally, as illustrated, the Annotation 730 corresponds to the cohort (or cohort qualifier) that the statement applies to.

In the illustrated embodiment, each of the relevant factors (e.g., Annotations 710, 715, 720, 725, and 730) are included within the same Excerpt 705. In embodiments, however, one or more of the relevant pieces of information can be located outside of the Excerpt 705. For example, in an embodiment, the cohort may be specified elsewhere in the document, and not explicitly given in the Excerpt 705. Similarly, one or more of the therapies or outcomes can be given elsewhere. For example, suppose the statement included "therapy Y led to the best results for the patients included in this study." In such an embodiment, the Extraction Component 330 and/or Annotation Component 335 can look elsewhere to determine the other therapy, the cohort, and the particular outcome type. Further, in an embodiment, the excerpt may only summarize one of the therapies in question and the Annotation Component 335 may look elsewhere to determine the complete definition of the therapy. For example, an excerpt may refer to "drug X-based therapy," where all of the components of this therapy are defined elsewhere in the document.

For example, the other therapies being tested may be listed in an introductory section, the cohort can be determined based on analyzing the patients involved, and the outcome of interest can be identified based on other sections of the document. In some embodiments, if the relevant information is not contained within the Excerpt 705, the confidence or weight of the comparative statement is reduced. In some embodiments, the Extraction Component 330 and/or Annotation Component 335 identify both the cohort (e.g., the patient population being studied) as well as cohort qualifiers (e.g., additional restrictions or limitations defining the group to whom the comparison is relevant). In one embodiments, the relevant cohort can identified based on other portions of the document (e.g., based on the abstract or study definitions). For example, a section of the document can indicate that the patients studied included females, aged 65-80, with hypertension. Additionally, the cohort qualifier ("high grade serious ovarian cancer") further restricts or limits the cohort to which the comparison is applicable.

As illustrated, the Cognitive Interpretation Component 205 (e.g., the Sentiment Component 340) then generates a RES 240A, based on the comparative statement. In the illustrated embodiment, as indicated by the arrow from Drug A to Drug B, the RES 240A indicates the relative efficacy of Drug A, as compared to Drug B. As illustrated, the sentiment is "positive," indicating that Drug A is better than Drug B with respect to the indicated cohort and the indicated outcome. Further, as illustrated, the outcome is "progression-free survival," and the cohort is individuals with "high grade serious ovarian cancer." As discussed above, in embodiments, this cohort can include additional attributes or definition, in combination with the cohort qualifiers found in the statement. Additionally, in the illustrated embodiment, the RES 240A includes a weight. In embodiments, this weight is based on a variety of factors, including the confidence of the NLP, the publication characteristics of the document, and the like.

Figure 7B:
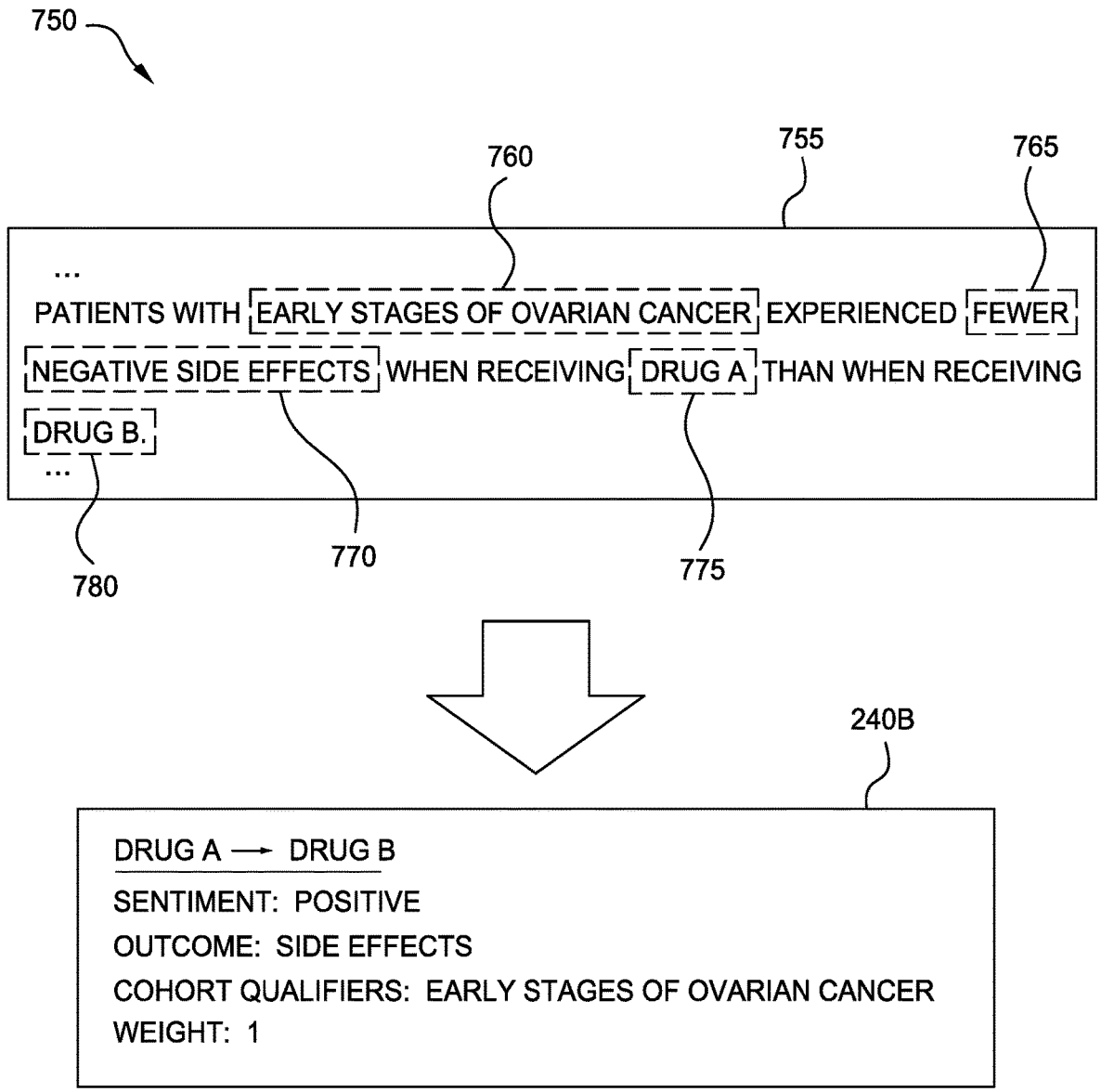

FIG. 7B illustrates a workflow 750 for determining the efficacy for a therapy, as compared to a different therapy, according to one embodiment disclosed herein. In the illustrated workflow 750, a comparative statement (included in an Excerpt 755) is annotated with Annotations 760, 765, 770, 775, and 780. As illustrated by the ellipses above and below the comparative statement, the original document can be any size or length. In an embodiment, the Excerpt 755 was extracted from a document (e.g., by the Extraction Component 330) based on determining that it included a comparative statement.

In an embodiment, the Excerpt 755 was annotated by the Annotation Component 335, using one or more NLP techniques. In the illustrated embodiment, Annotations 775 and 780 indicate the therapies mentioned or implicated by the statement. In one embodiment, these therapies are identified using the NLP models or techniques. Further, as illustrated, the Annotation 770 indicates the outcome of interest (also referred to as the type) that is relevant to the statement. That is, in the illustrated embodiment, the Excerpt 755 discusses the relative efficacy of Drug A and Drug B, with respect to negative side effects. Additionally, the Annotation 765 indicates the comparator (also referred to as qualifier or type qualifier), which indicates the comparison or statement being made (e.g., that the outcome, negative side effects, was "fewer."). Finally, as illustrated, the Annotation 760 corresponds to the cohort (or cohort qualifier) that the statement applies to.

As illustrated, the Cognitive Interpretation Component 205 (e.g., the Sentiment Component 340) then generates a RES 240B, based on the comparative statement. In the illustrated embodiment, as indicated by the arrow from Drug A to Drug B, the RES 240B indicates the relative efficacy of Drug A, as compared to Drug B. As illustrated, the sentiment is "positive," indicating that Drug A is better than Drug B with respect to the indicated cohort and the indicated outcome. That is, because the outcome itself is negative, the Sentiment Component 340 determines that a "worse" result in terms of the number or magnitude of side effects is, in fact, a positive result. Further, as illustrated, the outcome is "toxicity," and the cohort is individuals with "early stages of ovarian cancer." Additionally, in the illustrated embodiment, the RES 240B includes a weight. In embodiments, this weight is based on a variety of factors, including the confidence of the NLP, the publication characteristics of the document, and the like.

Figure 8:
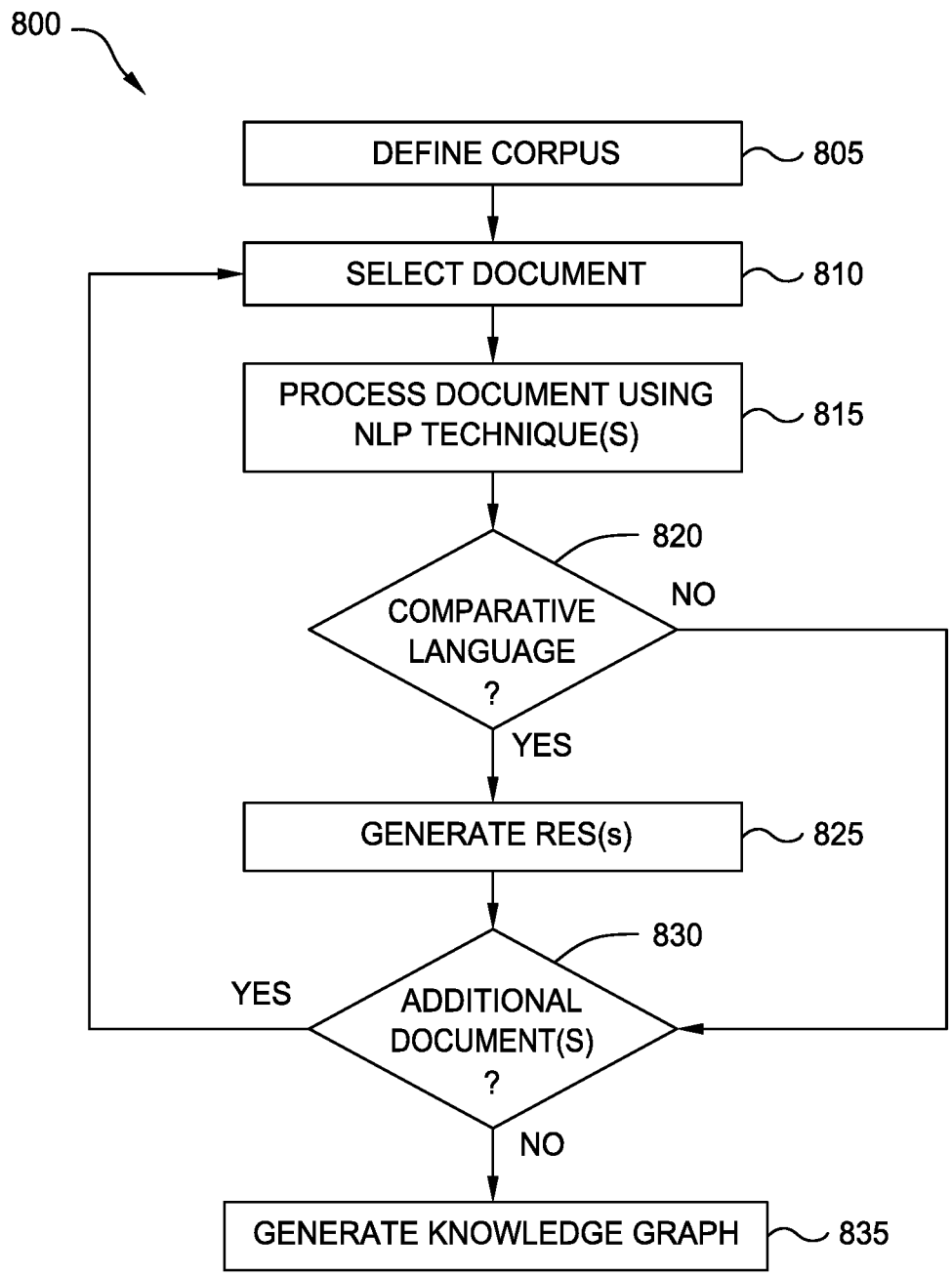
FIG. 8 illustrates a flow diagram illustrating a method for determining relative efficacies of various therapies, according to one embodiment disclosed herein.

FIG. 8 is a flow diagram illustrating a method 800 for determining relative efficacies of various therapies, according to one embodiment disclosed herein. The method 800 begins at block 805, where the Cognitive Interpretation Application 205 defines the relevant corpus. In one embodiment, this is based on a corpus indicated by the user or administrator. In some embodiments, the Cognitive Interpretation Application 205 receives one or more search terms, and builds the relevant corpus by searching or querying a larger corpus based on the search terms. In some embodiments, the Cognitive Interpretation Application 205 determines a set of documents in the identified corpus or sub-corpus that have not yet been processed or ingested. For example, in one embodiment, a user can indicate a disorder or search term, and the Cognitive Interpretation Application 205 can first identify documents relating to the indicated terms, and then identify documents in the corpus that have not already been processed and ingested. In this way, the Cognitive Interpretation Application 205 can selectively analyze new documents in order to update and refine the knowledge base. Once the relevant corpus has been defined, the method 800 proceeds to block 810.

At block 810, the Cognitive Interpretation Application 205 selects a document from the corpus. At block 815, the Cognitive Interpretation Application 205 processes the all or a portion of the selected document using one or more NLP techniques. As discussed above, in some embodiments, the Cognitive Interpretation Application 205 analyzes specified portions of each document. In some embodiments, if no comparisons are found (or if one or more identified comparative statements are missing information or detail), the Cognitive Interpretation Application 205 can process additional sections or text. In one embodiment, the Cognitive Interpretation Application 205 also annotates the extracted excerpts during block 815. The method 800 then proceeds to block 820.

At block 820, the Cognitive Interpretation Application 205 determines whether the selected document (or the portion that was analyzed) includes any comparative statements. If so, the method 800 continues to block 825. If not, the method 800 proceeds to block 830. At block 825, the Cognitive Interpretation Application 205 generates one or more RESs 240 for each of the identified comparative statements found. The method 800 then continues to block 830. At block 830, the Cognitive Interpretation Application 205 determines whether there is at least one additional document in the corpus that is yet to be processed. If so, the method 800 returns to block 810. Otherwise, the method 800 continues to block 835, where the Knowledge Graph Component 210 generates (or updates) a knowledge graph.

Figure 9:
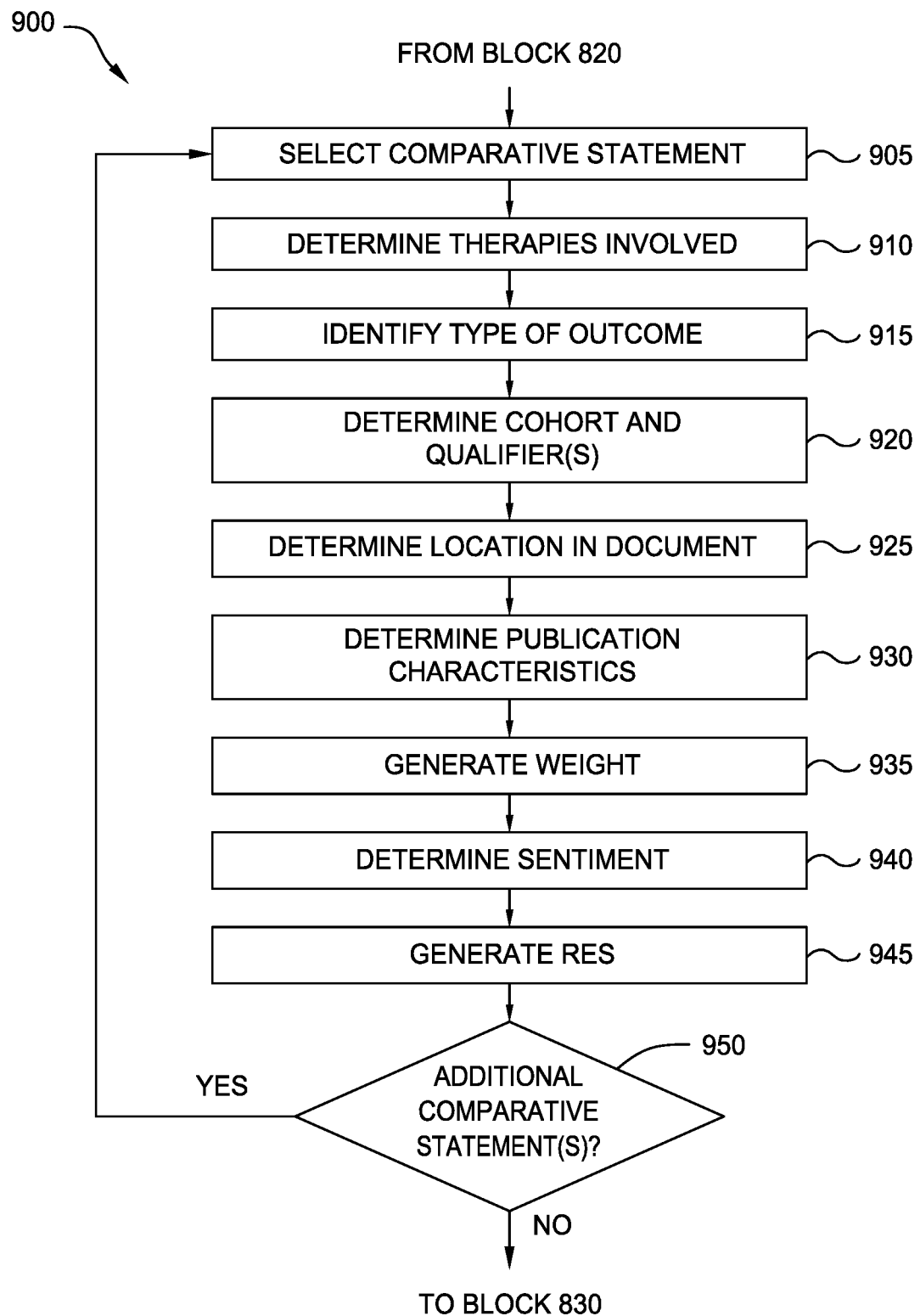
FIG. 9 is a flow diagram illustrating a method for generating relative efficacy structures summarizing comparisons between therapies, according to one embodiment disclosed herein.

FIG. 9 is a flow diagram illustrating a method 900 for generating RESs 240 summarizing comparisons between therapies, according to one embodiment disclosed herein. In one embodiment, the method 900 provides additional detail for block 825 in FIG. 8. The method 900 begins at block 905, where the Cognitive Interpretation Application 205 selects one of the comparative statements that were identified in the selected document. At block 910, the Cognitive Interpretation Application 205 identifies the therapies that are implicated by the selected statement. In one embodiment, the Cognitive Interpretation Application 205 utilizes NLP techniques to identify the relevant therapies. As discussed above, in some embodiments, the Cognitive Interpretation Application 205 parses other sections of the document, and/or other documents and data, in order to disambiguate any unknown or uncertain terms (e.g., ambiguous phrases or acronyms). The method 900 then continues to block 915.

At block 915, the Cognitive Interpretation Application 205 identifies the type of outcome the statement is addressing. That is, the Cognitive Interpretation Application 205 determines the particular outcome or effect that the selected statement is referring to. For example, in a medical embodiment, the outcomes can include overall survival, progression-free survival, remission, cure, death, complications, side effects, and the like. The method 900 then continues to block 920, where the Cognitive Interpretation Application 205 determines the cohort and/or cohort qualifiers that are relevant to the statement. For example, the cohort may be determined based on the patients being studied (e.g., as indicated by criteria used by the study authors when enrolling patients), and the cohort qualifiers can include any additional limitations included in the statement (e.g., "only patients above 65 saw a significant improvement.").

At block 925, the Cognitive Interpretation Application 205 determines the location in the selected document where the selected comparative statement was found. In one embodiment, block 925 comprises determining the section that the statement was in. In an embodiment, the sections are identified based on defined headings, metadata tags, and the like. In some embodiments, the weight of the generated RES 240 is adjusted based on the location. That is, in one embodiment, each section is associated with a respective weight or scale. For example, in one embodiment, the conclusion and abstract sections may be afforded higher weight than the general discussion section.

The method 900 then continues to block 930, where the Cognitive Interpretation Application 205 determines publication characteristics of the selected document that the statement was found in. For example, in one embodiment, the publication characteristics include a date when the document was published, the identity of the publisher, whether it has been peer-reviewed, and the like. In some embodiments, the publication characteristics also include the location in the document where the comparative statement was found. At block 935, the Cognitive Interpretation Application 205 generates a weight for the RES 240 based on the publication characteristics, and/or the determined location. In some embodiments, the Cognitive Interpretation Application 205 also considers any confidence values generated by the NLP models when parsing the text. Further, in one embodiment, the weight is based in part on the strength of the comparator used (e.g., whether the treatment is "slightly better" or "far superior").

The method 900 then continues to block 940, where the Cognitive Interpretation Application 205 determines the sentiment of the statement. In an embodiment, as discussed above, the Cognitive Interpretation Application 205 utilizes NLP to classify the statement as positive, negative, or neutral. Finally, at block 945, the Cognitive Interpretation Application 205 generates a RES 240 for the selected comparative statement based on the determined attributes, sentiment, and weight. At block 950, the Cognitive Interpretation Application 205 determines whether there is at least one additional comparative statement found in the document. If so, the method 900 returns to block 905. Otherwise, the method 900 terminates.

Figure 10:
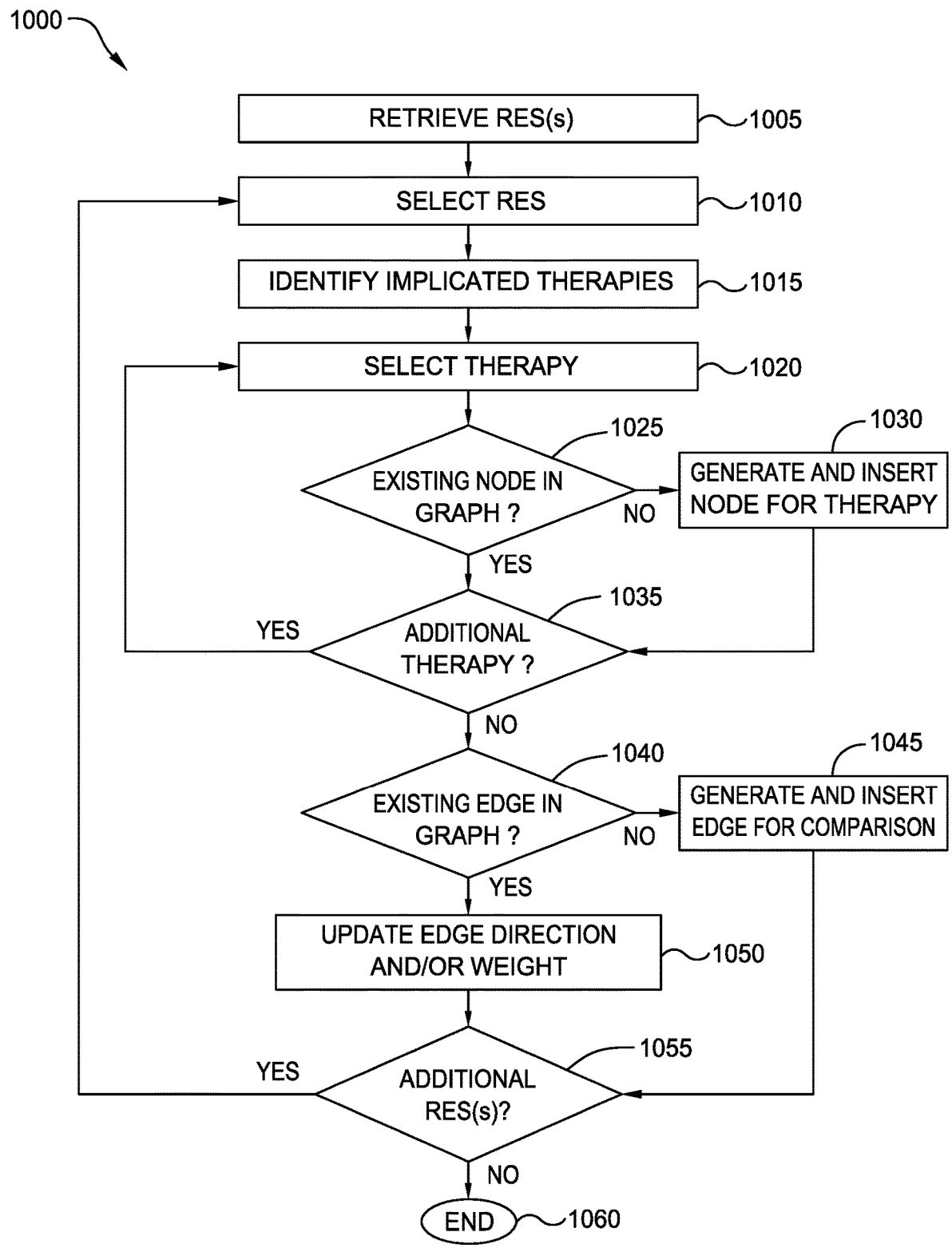
FIG. 10 is a flow diagram illustrating a method for generating a knowledge graph based on generated relative efficacy structures, according to one embodiment disclosed herein.

FIG. 10 is a flow diagram illustrating a method 1000 for generating a knowledge graph based on generated relative efficacy structures, according to one embodiment disclosed herein. The method 1000 begins at block 1005, where the Knowledge Graph Component 210 retrieves one or more RES(s) 240 that were generated by the Cognitive Interpretation Application 205. At block 1010, the Knowledge Graph Component 210 selects one of the RESs 240. The method 1000 then proceeds to block 1015, where the Knowledge Graph Component 210 identifies the therapies that are indicated by the selected RES 240. That is, the Knowledge Graph Component 210 determines which therapies are compared in the RES 240. At block 1020, the Knowledge Graph Component 210 selects one of these identified therapies.

The method 1000 continues to block 1025, where the Knowledge Graph Component 210 determines whether there is an existing node in the knowledge graph for the selected therapy. As discussed above, in an embodiment, each node in the knowledge graph corresponds to a therapy. In some embodiments, a therapy can include a combination of treatments or mediations (e.g., a drug as well as physical therapy). If the selected therapy is already represented in the knowledge graph, the method 1000 continues to block 1035. If the selected therapy is not yet in the knowledge graph, the method 1000 proceeds to block 1030, where the Knowledge Graph Component 210 generates and inserts a new node into the graph to represent the selected therapy. The method 1000 then continues to block 1035.

At block 1035, the Knowledge Graph Component 210 determines whether there are additional therapies in the selected RES 240. If so, the method 1000 returns to block 1020. Otherwise, the method 1000 continues to block 1040. In the illustrated embodiment, the Knowledge Graph Component 210 analyzes each therapy, and generates new nodes for each. In some embodiments, the knowledge graph is already constructed using a known or defined set of therapies. In such an embodiment, the Knowledge Graph Component 210 does not generate and insert new nodes. In some embodiments, in addition to an existing set of therapies, the Knowledge Graph Component 210 can further generate and insert nodes representing new therapies or new combinations of treatments that are identified in the RES 240.

In one embodiment, each node in the knowledge graph can be connected to zero or more other nodes, based on whether a comparison has been identified between the corresponding therapies. For example, in one embodiment, if two therapies have not been directly compared in the published literature, there will be no link or connection between the corresponding nodes. If, however, the therapies have been compared at least once, there will be an edge or connection between them. In some embodiments, each edge includes a number of dimensions indicating the directionality, the cohort(s) the edge applies to, the outcome(s) the edge applies to, and the like. For example, in such an embodiment, an edge may indicate that treatment A is better than treatment B, with respect to overall survival, in patients over 65. For patients under 65, however, there may be no edge or connection (if the therapies have not been compared for patients under 65), or there may be a link indicating that treatment B is better than treatment A. Similarly, with respect to a different outcome (such as progression-free survival or side effects), there may be no link, or a different link or connection may indicate that treatment B is better than treatment A. In some embodiments, the knowledge graph is constructed with a single edge connecting each pair of therapies, where that edge identifies all documents and/or RESs 240 that included a statement comparing the respective therapies. In another embodiment, the graph can include a respective edge to represent each respective RES 240 that is relevant to the respective pair of therapies.

In some embodiments, each edge in the graph is associated with a respective weight. This weight can be based on a variety of factors, including the number of times the relationship has been identified (e.g., the number of RESs 240 associated with the particular edge), the confidence or weight of each of those RESs 240, and the like. In some embodiments, as additional RESs 240 indicate the same relative efficacy (e.g., that one therapy is better than the other), the weight or strength of the edge is progressively strengthened. If, however, a RES 240 indicates the opposite comparison (e.g., that the first therapy is worse than the other), the weight or strength of the edge is reduced. In this way, each connection in the graph indicates an overall relative efficacy of the therapies, along with an associated strength or confidence in the accuracy of the comparison.

At block 1040, the Knowledge Graph Component 210 determines whether there is an existing edge in the knowledge graph representing the relationship indicated by the selected RES 240. That is, in an embodiment, the Knowledge Graph Component 210 determines whether there is any link or connection between the identified therapies, with respect to the indicated cohort and outcome, regardless of the directionality of the relationship (e.g., regardless of whether the existing link matches the determined relative efficacy in the RES 240). In an embodiment, there may be any number of connections between the identified therapies with respect to other cohorts or other outcomes. The determination at block 1040, however, is specific to the particular cohort and outcome specified in the RES 240.

In some embodiments, a particular RES 240 can include multiple comparisons. For example, if a statement included that treatment A was superior than all known treatments, the Cognitive Interpretation Application 205 can parse or analyze existing literature (or one or more knowledge graphs) to identify known treatments with respect to the disorder, cohort, and outcome. In such an embodiment, the RES 240 can include an indication of each of these known treatments. In other embodiments, a separate RES 240 is created for each of the comparisons (e.g., for each of the known treatments). In an embodiment, if the RES 240 includes comparisons to multiple therapies, the process discussed below (and reflected by blocks 1040, 1045, and 1050) is repeated for each.

If the Knowledge Graph Component 210 determines, at block 1040, that there is no edge in the graph representing the comparison, with respect to the identified cohort and outcome, the method 1000 continues to block 1045, where the Knowledge Graph Component 210 generates and inserts one. In one embodiment, the directionality of the new edge is based on the sentiment reflected in the selected RES 240 (e.g., positive, negative, or neutral). Further, in an embodiment, the initial weight or strength of the new edge is based on the weight or confidence of the RES 240. In this way, the knowledge graph is updated to reflect that the published literature includes a direct comparison between the therapies, and indicates the relative efficacy of the therapies (e.g., based on the directionality of the edge).

If the Knowledge Graph Component 210 determines, at block 1040, that an edge already exists for the indicated comparison, with respect to the specified cohort and outcome, the method 1000 continues to block 2050, where the Knowledge Graph Component 210 updates the weight and/or direction of the identified edge. In some embodiments, the Knowledge Graph Component 210 instead inserts a new edge, depending on the particular design that will be used to represent multiple comparisons between two treatments in the knowledge graph. As discussed above, in one embodiment, this updating includes adjusting the weight of the edge based on the weight and directionality of the selected RES 240. In an embodiment, if the sentiment reflected by the RES 240 is in the same direction as the existing edge (e.g., the RES 240 and the edge agree that one treatment is superior), the weight or strength is increased. If the directions are opposite, the weight is decreased. Similarly, in one embodiment, if the selected RES 240 has a neutral sentiment (indicating that the therapies are equally effective), the weight of the edge is reduced, regardless of which direction it currently points. If the edge is already neutral, a neutral weight or strength can be increased, indicating that there is additional evidence that the therapies are equally effective.

In one embodiment, the amount that the edge strength is changed is dependent on the magnitude of the confidence or weight associated with the RES 240. If the RES 240 is associated with a high weight, the strength of the edge will be adjusted a greater amount than if the weight of the RES 240 was low. In one embodiment, if the weight falls below a predefined threshold (e.g., within a defined distance from zero), the edge is removed from the graph, indicating that there is no medical consensus regarding the relationship or relative efficacy. In other embodiments, the edge is updated to have no direction, reflecting that there is no solid consensus, and results are mixed (e.g., indicating that the comparison has been studied, but that there is no strong evidence supporting either therapy as more effective than the other). In some embodiments, this edge is retained with a low weight or strength, and is assigned a neutral sentiment to indicate that neither therapy is clearly superior to the other.

Similarly, in some embodiments, if an edge is neutral (or close to neutral) and the weight adjustment would cause the weight to be negative, the direction of the edge is switched, indicating a (potentially weak) new consensus that the relative efficacy of the treatments is reversed from the previously-understood comparison. In some embodiments, each edge in the graph is associated with a directionality as well as a weight or strength of the edge (representing the strength of the evidence). The method 1000 then proceeds to block 2055, where the Knowledge Graph Component 210 determines whether there is at least one additional RES 240 that has not been analyzed and ingested into the knowledge graph. If so, the method 1000 returns to block 1010 to select a next RES 240. Otherwise, the method 1000 terminates at block 1060. In this way, the Knowledge Graph Component 210 can update and refine the knowledge graph based on new therapies and studies. In embodiments, the knowledge graph is a multi-dimensional representation of the medical consensus as to relative efficacies of any number of therapies, with respect to any combination of particular cohorts and outcomes. Advantageously, embodiments of the present disclosure enable the graph to be continuously and rapidly updated when new published literature becomes available, such that the knowledge graph represents the most up-to-date and accurate representation possible. Further, because of the high-dimensionality of the graph (e.g., because the relative efficacies differ based on the individual cohort and outcome), the knowledge graph provides additional data that is far more granular, and is not otherwise available to healthcare providers.

In some embodiments, the knowledge graph can be accessed and searched by healthcare providers in order to determine optimal treatments for a particular patient. For example, in an embodiment, the provider can search the knowledge graph (e.g., using the User Interface 380 of the Client Device 355) to identify therapies and/or relative efficacies that are relevant to the cohort to which the patient belongs. That is, in an embodiment, the knowledge graph can be parsed to identify comparisons that are relevant to a patient in a particular cohort (e.g., having a particular set of attributes). In some embodiments, the provider can also filter, sort, or search the knowledge graph based on the desired outcome. In one embodiment, based on these relative efficacies, the therapies can be scored and ranked, in order to identify the most optimal therapy. This allows the provider to make improved decisions with respect to treating the patient.

In some embodiments, the outcomes types are associated with a predefined hierarchy. That is, some outcomes (e.g., progression-free survival) may be considered more important than other outcomes (e.g., side effects), and therefore be weighted more heavily when aggregating the relative efficacies with respect to each outcome in order to determine an overall relative efficacy (e.g., an overall optimal or best therapy, with respect to all outcomes). In such an embodiment, the ranking or scoring of the therapies may take into account the relative efficacies, as well as the importance or weight of the particular outcome. That is, although a first therapy may be the best with respect to side effects, it may be given a lower score than a second therapy that is better with respect to survival.

Although not illustrated, in some embodiments, the Knowledge Graph Component 210 can further generate nodes for which there are no existing comparisons. For example, if a paper or article includes a study of a particular therapy, but does not include any comparison to other therapies, the Knowledge Graph Component 210 can generate a node for the therapy, without necessarily connecting the node to any other therapies. Further, in some embodiments, the Knowledge Graph Component 210 includes an indication as to the efficacy of each therapy. For example, in such an embodiment, the Cognitive Interpretation Application 205 can determine the overall efficacy for each particular therapy, in addition to determining the relative efficacies of therapies, as compared to each other. This information can then be included in the corresponding node in the knowledge graph. In embodiments, the efficacy can include a percentage of patients who the therapy helped, and/or an amount that the therapy helped.

Figure 11:
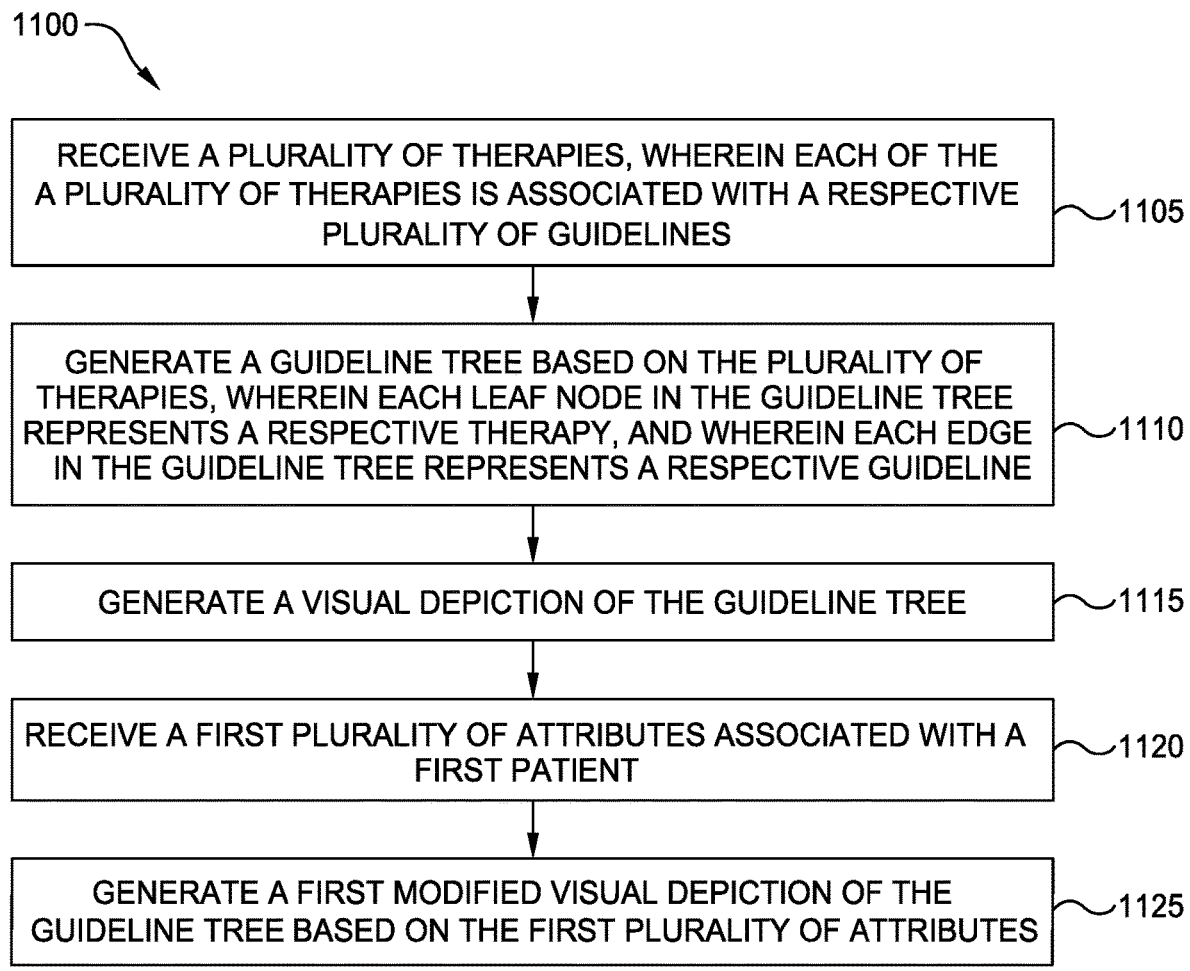
FIG. 11 is a flow diagram illustrating a method for generating dynamic visualizations using a guideline tree, according to one embodiment disclosed herein.

FIG. 11 is a flow diagram illustrating a method 1100 for generating dynamic visualizations using a guideline tree, according to one embodiment disclosed herein. The method 1100 begins at block 1105, where the Guideline Tree Application 390 receives a plurality of therapies, wherein each of the plurality of therapies is associated with a respective plurality of guidelines. At block 1110, the Guideline Tree Application 390 generates a guideline tree based on the plurality of therapies, wherein each leaf node in the guideline tree represents a respective therapy, and wherein each edge in the guideline tree represents a respective guideline. The method 1100 then proceeds to block 1115, where the Guideline Tree Application 390 generates a visual depiction of the guideline tree. Further, at block 1120, the Guideline Tree Application 390 receives a first plurality of attributes associated with a first patient. Finally, at block 1125, the Guideline Tree Application 390 generates a first modified visual depiction of the guideline tree based on the first plurality of attributes.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Guideline Tree Application 390) or related data available in the cloud. For example, the Guideline Tree Application 390 could execute on a computing system in the cloud and generate guideline trees for visualization. In such a case, the Guideline Tree Application 390 could evaluate medical evidence to generate guidelines trees, and store the trees at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
receiving a plurality of therapies, wherein each respective therapy of the plurality of therapies is associated with a respective plurality of guidelines indicating guidance regarding whether the respective therapy is appropriate based on patient attributes;
generating a guideline tree based on the plurality of therapies, the guideline tree comprising:
a set of leaf nodes, wherein each respective leaf node represents a respective therapy,
a set of internal nodes, wherein the set of internal nodes represent attributes that inform treatment decisions, based on the respective pluralities of guidelines, and
a set of edges, wherein each respective edge represents a respective guideline;
generating a visual depiction of the guideline tree, wherein the visual depiction depicts the set of leaf nodes, the set of internal nodes, and the set of edges arranged as a tree;
receiving a first plurality of attributes associated with a first patient;
generating a first modified visual depiction of the guideline tree based on the first plurality of attributes, wherein the first modified visual depiction visually emphasizes a subset of the guideline tree;
outputting the first modified visual depiction via a graphical user interface (GUI);
receiving a second plurality of attributes associated with the first patient;
dynamically generating a second modified visual depiction of the guideline tree based on the second plurality of attributes, wherein the second modified visual depiction emphasizes a first path from a root node to a leaf node associated with a first suggested therapy based on the first plurality of attributes, and a second path from the root node to a leaf node associated with a second suggested therapy based on the second plurality of attributes;
generating a dynamic visualization of the guideline tree, wherein the dynamic visualization includes an animation comprising a morph between the first modified visual depiction and the second modified visual depiction;
generating a knowledge graph based on a plurality of Relative Efficacy Structures (RESs), wherein:
each RES is generated from a respective comparison statement between at least two identified therapies with respect to at least one outcome,
the respective comparison statement is identified by using one or more natural language processing (NLP) techniques in one or more natural language texts from a corpus of medical literature, and
the knowledge graph comprises a plurality of nodes and a plurality of edges, wherein:
each node represents a therapy associated with one or more of the RESs, and
each edge connects at least two of the nodes and represents a relative efficacy between the at least two therapies represented by the at least two nodes based on the one or more RESs;

determining an optimal therapy identified in the knowledge graph for the first patient is different from the first suggested therapy, wherein the optimal therapy corresponds to a first node of the plurality of nodes in the knowledge graph, the first suggested therapy corresponds to a second node of the plurality of nodes in the knowledge graph, and an edge of the plurality of edges in the knowledge graph indicates that the first node has a higher efficacy than the second node with respect to at least one outcome of at least one of the one or more RESs;

updating the dynamic visualization by generating a new modified visual depiction of the guideline tree to emphasize a leaf node corresponding to the optimal therapy; and outputting the dynamic visualization via a graphical user interface (GUI).

2. The method of claim 1, the method further comprising:
receiving a third plurality of attributes associated with a second patient; and
generating a third modified visual depiction of the guideline tree based on the third plurality of attributes, wherein the third modified visual depiction emphasizes a first path from a root node to a leaf node associated with a first suggested therapy for the first patient, and a second path from the root node to a leaf node associated with a second suggested therapy for the first patient, and a third path from the root node to a leaf node associated with a third suggested therapy for the second patient.

3. The method of claim 1, the method further comprising:
analyzing the knowledge graph to identify the optimal therapy, of the plurality of therapies, for the first patient.

4. The method of claim 1, the method further comprising:
identifying a first path in the guideline tree beginning at a root node and ending at the leaf node corresponding to the first suggested therapy;
identifying a second path in the guideline tree beginning at the root node and ending at the leaf node corresponding to the optimal therapy;
determining a node in the guideline tree where the first path and the second path diverge; and
providing an indication of the determined node.

5. The method of claim 1, the method further comprising:
identifying a cohort of similar patients, based on the first plurality of attributes associated with the first patient;
analyzing one or more electronic medical records associated with at least one similar patient in the cohort of similar patients to determine a preferred therapy; and
upon determining that the preferred therapy is different from the first suggested therapy, generating a third modified visual depiction of the guideline tree to emphasize a leaf node corresponding to the preferred therapy.

6. The method of claim 1, the method further comprising determining a set of edges in the guideline tree based on the first plurality of attributes, wherein the first modified visual depiction of the guideline tree further emphasizes the set of edges, and wherein the set of edges corresponds to a path in the guideline tree beginning at a root node and ending at the leaf node corresponding to the first suggested therapy.

7. A computer-readable storage medium having computer-readable program code embodied therewith, the computer-readable program code executable by one or more computer processors to perform an operation comprising:

receiving a plurality of therapies, wherein each respective therapy of the plurality of therapies is associated with a respective plurality of guidelines indicating guidance regarding whether the respective therapy is appropriate based on patient attributes;

generating a guideline tree based on the plurality of therapies, the guideline tree comprising:
a set of leaf nodes, wherein each respective leaf node represents a respective therapy,
a set of internal nodes, wherein the set of internal nodes represent attributes that inform treatment decisions, based on the respective pluralities of guidelines, and
a set of edges, wherein each respective edge represents a respective guideline;

generating a visual depiction of the guideline tree, wherein the visual depiction depicts the set of leaf nodes, the set of internal nodes, and the set of edges arranged as a tree;

receiving a first plurality of attributes associated with a first patient;

generating a first modified visual depiction of the guideline tree based on the first plurality of attributes, wherein the first modified visual depiction visually emphasizes a subset of the guideline tree;

outputting the first modified visual depiction via a graphical user interface (GUI);

receiving a second plurality of attributes associated with the first patient;

dynamically generating a second modified visual depiction of the guideline tree based on the second plurality of attributes, wherein the second modified visual depiction emphasizes a first path from a root node to a leaf node associated with a first suggested therapy based on the first plurality of attributes, and a second path from the root node to a leaf node associated with a second suggested therapy based on the second plurality of attributes;

generating a dynamic visualization of the guideline tree, wherein the dynamic visualization includes an animation comprising a morph between the first modified visual depiction and the second modified visual depiction;

generating a knowledge graph based on a plurality of Relative Efficacy Structures (RESs), wherein:
each RES is generated from a respective comparison statement between at least two identified therapies with respect to at least one outcome,
the respective comparison statement is identified by using one or more natural language processing (NLP) techniques in one or more natural language texts from a corpus of medical literature, and
the knowledge graph comprises a plurality of nodes and a plurality of edges, wherein:
each node represents a therapy associated with one or more of the RESs, and
each edge connects at least two of the nodes and represents a relative efficacy between the at least two therapies represented by the at least two nodes based on the one or more RESs;

determining an optimal therapy identified in the knowledge graph for the first patient is different from the first suggested therapy, wherein the optimal therapy corresponds to a first node of the plurality of nodes in the knowledge graph, the first suggested therapy corresponds to a second node of the plurality of nodes in the knowledge graph, and an edge of the plurality of edges in the knowledge graph indicates that the first node has a higher efficacy than the second node with respect to at least one outcome of at least one of the one or more RESs;

updating the dynamic visualization by generating a new modified visual depiction of the guideline tree to emphasize a leaf node corresponding to the optimal therapy; and outputting the dynamic visualization via a graphical user interface (GUI).

8. The computer-readable storage medium of claim 7, the operation further comprising:

identifying a first path in the guideline tree beginning at a root node and ending at the leaf node corresponding to the first suggested therapy;

identifying a second path in the guideline tree beginning at the root node and ending at the leaf node corresponding to the optimal therapy;

determining a node in the guideline tree where the first path and the second path diverge; and providing an indication of the determined node.

9. The computer-readable storage medium of claim 7, the operation further comprising:

identifying a cohort of similar patients, based on the first plurality of attributes associated with the first patient;

analyzing one or more electronic medical records associated with at least one similar patient in the cohort of similar patients to determine a preferred therapy; and upon determining that the preferred therapy is different from the first suggested therapy, generating a third modified visual depiction of the guideline tree to emphasize a leaf node corresponding to the preferred therapy.

10. The computer-readable storage medium of claim 7, the operation further comprising determining a set of edges in the guideline tree based on the first plurality of attributes, wherein the first modified visual depiction of the guideline tree further emphasizes the set of edges, and wherein the set of edges corresponds to a path in the guideline tree beginning at a root node and ending at the leaf node corresponding to the first suggested therapy.

11. The computer-readable storage medium of claim 7, the operation further comprising:

analyzing the knowledge graph to identify the optimal therapy, of the plurality of therapies, for the first patient.

12. A system comprising:

one or more computer processors; and a memory containing a program which when executed by the one or more computer processors performs an operation, the operation comprising:

receiving a plurality of therapies, wherein each respective therapy of the plurality of therapies is associated with a respective plurality of guidelines indicating guidance regarding whether the respective therapy is appropriate based on patient attributes;

generating a guideline tree based on the plurality of therapies, the guideline tree comprising:

a set of leaf nodes, wherein each respective leaf node represents a respective therapy, a set of internal nodes, wherein the set of internal nodes represent attributes that inform treatment decisions, based on the respective pluralities of guidelines, and a set of edges, wherein each respective edge represents a respective guideline;

generating a visual depiction of the guideline tree, wherein the visual depiction depicts the set of leaf nodes, the set of internal nodes, and the set of edges arranged as a tree;

receiving a first plurality of attributes associated with a first patient;

generating a first modified visual depiction of the guideline tree based on the first plurality of attributes, wherein the first modified visual depiction visually emphasizes a subset of the guideline tree;

outputting the first modified visual depiction via a graphical user interface (GUI);

receiving a second plurality of attributes associated with the first patient;

dynamically generating a second modified visual depiction of the guideline tree based on the second plurality of attributes, wherein the second modified visual depiction emphasizes a first path from a root node to a leaf node associated with a first suggested therapy based on the first plurality of attributes, and a second path from the root node to a leaf node associated with a second suggested therapy based on the second plurality of attributes;

generating a dynamic visualization of the guideline tree, wherein the dynamic visualization includes an animation comprising a morph between the first modified visual depiction and the second modified visual depiction;

generating a knowledge graph based on a plurality of Relative Efficacy Structures (RESs), wherein:

each RES is generated from a respective comparison statement between at least two identified therapies with respect to at least one outcome, the respective comparison statement is identified by using one or more natural language processing (NLP) techniques in one or more natural language texts from a corpus of medical literature, and the knowledge graph comprises a plurality of nodes and a plurality of edges, wherein:

each node represents a therapy associated with one or more of the RESs, and each edge connects at least two of the nodes and represents a relative efficacy between the at least two therapies represented by the at least two nodes based on the one or more RESs;

determining an optimal therapy identified in the knowledge graph for the first patient is different from the first suggested therapy, wherein the optimal therapy corresponds to a first node of the plurality of nodes in the knowledge graph, the first suggested therapy corresponds to a second node of the plurality of nodes in the knowledge graph, and an edge of the plurality of edges in the knowledge graph indicates that the first node has a higher efficacy than the second node with respect to at least one outcome of at least one of the one or more RESs;

updating the dynamic visualization by generating a new modified visual depiction of the guideline tree to emphasize a leaf node corresponding to the optimal therapy; and outputting the dynamic visualization via a graphical user interface (GUI).

13. The system of claim 12, the operation further comprising:

analyzing the knowledge graph to identify the optimal therapy, of the plurality of therapies, for the first patient.

14. The system of claim 12, the operation further comprising:
- identifying a first path in the guideline tree beginning at a root node and ending at the leaf node corresponding to the first suggested therapy;
- identifying a second path in the guideline tree beginning at the root node and ending at the leaf node corresponding to the optimal therapy;
- determining a node in the guideline tree where the first path and the second path diverge; and
- providing an indication of the determined node.

15. The system of claim 12, the operation further comprising:
- identifying a cohort of similar patients, based on the first plurality of attributes associated with the first patient;
- analyzing one or more electronic medical records associated with at least one similar patient in the cohort of similar patients to determine a preferred therapy; and
- upon determining that the preferred therapy is different from the suggested therapy, generating a third modified visual depiction of the guideline tree to emphasize a leaf node corresponding to the preferred therapy.

16. The system of claim 12, the operation further comprising determining a set of edges in the guideline tree based on the first plurality of attributes, wherein the first modified visual depiction of the guideline tree further emphasizes the set of edges, and wherein the set of edges corresponds to a path in the guideline tree beginning at a root node and ending at the leaf node corresponding to the first suggested therapy.

* * * * *